United States Patent
Holekamp et al.

(10) Patent No.: US 12,161,586 B2
(45) Date of Patent: Dec. 10, 2024

(54) SYSTEMS FOR MANAGEMENT OF DRY EYE SYNDROME

(71) Applicant: DEL, LLC, Saint Louis, MO (US)

(72) Inventors: Nancy M. Holekamp, Saint Louis, MO (US); Rita E. Hindmon, Florissant, MO (US); Michael Stanton Korenfeld, Wildwood, MO (US)

(73) Assignee: DEL, LLC

( * ) Notice: Subject to any disclaimer, the term of this patent is extended or adjusted under 35 U.S.C. 154(b) by 1243 days.

(21) Appl. No.: 16/820,314

(22) Filed: Mar. 16, 2020

(65) Prior Publication Data

US 2021/0282638 A1     Sep. 16, 2021

(51) Int. Cl.
*A61F 9/007* (2006.01)
*A41G 5/02* (2006.01)
*A45D 44/00* (2006.01)
*A61F 2/10* (2006.01)

(52) U.S. Cl.
CPC .......... *A61F 9/00718* (2013.01); *A41G 5/02* (2013.01); *A45D 44/00* (2013.01); *A61F 2/10* (2013.01); *A61F 2250/0064* (2013.01)

(58) Field of Classification Search
CPC ............ A61F 2/10; A61F 2250/0064; A61F 9/00718; A61F 2250/0037; A61F 2250/0039; A61F 2250/0036; A41G 5/02; A45D 44/00

See application file for complete search history.

(56) References Cited

U.S. PATENT DOCUMENTS

| | | | |
|---|---|---|---|
| 3,590,828 | A | 7/1971 | Prewitt |
| 3,789,856 | A | 2/1974 | Bomba |
| D576,352 | S | 9/2008 | Brestoni |
| 8,424,542 | B1 | 4/2013 | Han |
| 8,701,685 | B2 | 4/2014 | Chipman |
| 8,881,744 | B2 | 11/2014 | McKinstry |
| 8,925,558 | B2 | 1/2015 | Johnson |
| 9,004,076 | B2 * | 4/2015 | Le .................. A41G 5/00 132/216 |

(Continued)

FOREIGN PATENT DOCUMENTS

| AU | 2015201939 | 11/2016 |
|---|---|---|
| CN | 204670589 | 9/2015 |

(Continued)

OTHER PUBLICATIONS

Amador, GJ et al., Eyelashes divert airflow to protect the eye, 2015, Journal of the Royal Society, vol. 12, Issue 105 (Year: 2015).*

(Continued)

*Primary Examiner* — Javier G Blanco
(74) *Attorney, Agent, or Firm* — FIG. 1 Patents

(57) ABSTRACT

In implementations of systems for management of dry eye syndrome, a palpebral fissure width is determined as a distance between a medial canthus and a lateral canthus of closed eyelids. An ideal eyelash length is generated based on the distance. Prostheses having the ideal eyelash length are attached to candidate eyelashes of an upper eyelid of the closed eyelids. The prostheses introduce a turbulence to airflow around a tear film which prevents the tear film from evaporating. Dry eye syndrome is managed by preventing the tear film from evaporating.

20 Claims, 13 Drawing Sheets

(56) References Cited

U.S. PATENT DOCUMENTS

| | | | |
|---|---|---|---|
| D758,009 S | 5/2016 | Berkos | |
| D788,985 S | 6/2017 | Hansen | |
| 9,993,334 B1* | 6/2018 | Loria | D01F 6/02 |
| 11,654,049 B2 | 5/2023 | Holekamp et al. | |
| 2005/0091727 A1 | 5/2005 | Fowler | |
| 2007/0227550 A1 | 10/2007 | Merszei | |
| 2012/0055499 A1* | 3/2012 | Sanbonmatsu | A41G 5/02 |
| | | | 132/201 |
| 2013/0042884 A1 | 2/2013 | Wilkinson | |
| 2013/0133681 A1 | 5/2013 | Chipman | |
| 2013/0152960 A1 | 6/2013 | Pays et al. | |
| 2014/0135914 A1 | 5/2014 | Conant | |
| 2014/0178118 A1 | 6/2014 | Wu et al. | |
| 2014/0277453 A1* | 9/2014 | Seidel | A61F 2/10 |
| | | | 623/15.11 |
| 2014/0331383 A1 | 11/2014 | Bially | |
| 2015/0173442 A1 | 6/2015 | Raouf | |
| 2016/0219959 A1 | 8/2016 | Chipman et al. | |
| 2016/0353861 A1 | 12/2016 | Carey | |
| 2017/0000204 A1 | 1/2017 | Wibowo | |
| 2017/0049172 A1 | 2/2017 | Ahn | |
| 2019/0117356 A1 | 4/2019 | Bartschi et al. | |
| 2021/0298952 A1 | 9/2021 | Holekamp et al. | |

FOREIGN PATENT DOCUMENTS

| | | |
|---|---|---|
| CN | 205193856 | 4/2016 |
| CN | 210696118 U | 6/2020 |
| JP | 2006297038 | 11/2006 |
| JP | 2012224390 | 11/2012 |
| JP | 2015081387 | 4/2015 |
| JP | 2016211095 | 12/2016 |
| JP | 6122634 | 4/2017 |
| KR | 101475003 | 12/2014 |
| KR | 200476330 | 2/2015 |
| WO | WO-2015031817 | 3/2015 |

OTHER PUBLICATIONS

Zou, S et al., How eyelashes can protect the eye through inhibiting ocular water evaporation: a chemical engineering perspective, 2019, Journal of the Royal Society, Interface, vol. 16, Issue 159 (Year: 2019).*

U.S. Appl. No. 16/828,721, "Non-Final Office Action", U.S. Appl. No. 16/828,721, Sep. 27, 2022, 25 pages.

U.S. Appl. No. 16/828,721,"Notice of Allowance", U.S. Appl. No. 16/828,721, Feb. 2, 2023, 11 pages.

Amador,"Eyelashes divert airflow to protect the eye", Mar. 2015, 12 pages.

Dartt,"Complexity of the tear film: Importance in homeostasis and dysfunction during disease", Dec. 2013, 6 pages.

Glaser,"Epidemiologic Analysis of Change in Eyelash Characteristics With Increasing Age in a Population of Healthy Women", Nov. 2014, pp. 1208-1213.

* cited by examiner

SYSTEMS FOR MANAGEMENT OF DRY EYE SYNDROME

BACKGROUND

Dry eye syndrome or keratoconjunctivitis sicca is a condition that manifests itself as an insufficiency of tear film. The tear film is a multi-layer fluid that covers and protects the outer surface of the human eye. These multiple layers include a thin lipid layer and an aqueous/mucin region which increases in mucin concentration closest to the cornea. The lipid layer includes both polar and non-polar lipids and prevents evaporation of the underlying aqueous/mucin region which forms the majority of the tear film.

The insufficiency of the tear film that is associated with dry eye syndrome may be due to a lack of adequate tear production or excessive tear evaporation. There are many potential causes of this insufficiency. For example, dry eye has been associated with certain medications, other medical conditions, environmental conditions, and blinking less frequently such as during long periods of concentration. Increased age is a metric associated with an increased risk of dry eye syndrome. Other metrics identified as increasing risk of dry eye include having a diet low in vitamin A, wearing contact lenses, and being female.

It has been hypothesized that mammalian eyelash length may be tangentially related to an increased risk for dry eye syndrome in some mammals such as mammal species native to dusty, arid environments. Amador G. J. et al. evaluated images depicting the open eyes of 22 species of mammals in *Eyelashes divert airflow to protect the eye*, J. R. Soc. Interface 12:20141294 (2015). Based on these images, Amador G. J. et al. suggested that a ratio of eyelash length to width of the mammalian eye of 0.35±0.15 is optimal for open eyes of mammals in walking locomotion having a walking gait. Amador G. J. et al. also evaluated four species of birds which have been observed to have eye-lining feathers similar to mammalian eyelashes. For these species of birds, an ideal ratio of feather length to width of the bird eye of 0.86 was observed.

Persons suffering from dry eye syndrome experience discomfort including pain and burning of the eyes. Additional complications from dry eye can include corneal surface abrasions, corneal ulcers, and decreased visual acuity (loss of vision). Due to the severity of these potential complications, management of the syndrome is of critical importance as soon as keratoconjunctivitis sicca is diagnosed.

Conventional techniques for management of dry eye syndrome include over-the-counter eye drops, prescription medications, punctal plugs, and surgical procedures. Over-the-counter eye drops are the most common form of dry eye management. These drops are designed to temporarily replace tear film with artificial tears. Compared to over-the-counter eye drops, prescription medications are generally more effective for management of dry eye syndrome. The prescription medications currently available are delivered as eye drops and are designed to increase tear production.

Punctal plugs and surgical procedures are less common conventional approaches as treatment for dry eye. Punctal plugs seal tear ducts and prevent the tear film from draining into the tear ducts. A surgical procedure such as a tarsorrhaphy which narrows the eyelid opening may be performed in some cases to help prevent evaporation of the tear film.

There are no existing processes or procedures for screening humans for dry eye syndrome. Instead, this disorder is identified based on the presence of its symptoms. Once identified, dry eye can be quantified using a variety of tests such as a survey, a Schirmer's test, a slit lamp test, a tear break up time test, a tear meniscus height test, etc. Despite the various conventional techniques for management of dry eye syndrome, the condition remains pervasive. This may be partially due to an increasing average life expectancy for humans worldwide coupled with an increased risk of suffering from dry eye associated with increased age.

SUMMARY

Systems and techniques are described for management of dry eye syndrome. In an example, a palpebral fissure width is determined as a distance between a medial canthus and a lateral canthus of closed eyelids. An ideal eyelash length is generated based on the distance. For example, the ideal eyelash length may be generated as approximately one-third of the distance.

A prosthesis having the ideal eyelash length is attached to a candidate eyelash of an upper eyelid of the closed eyelids. The prosthesis introduces a turbulence to airflow around a tear film which prevents the airflow from evaporating the tear film. By preventing the tear film from evaporating in this way, dry eye syndrome is managed safely and effectively.

This Summary introduces a selection of concepts in a simplified form that are further described below in the Detailed Description. As such, this Summary is not intended to identify essential features of the claimed subject matter, nor is it intended to be used as an aid in determining the scope of the claimed subject matter.

BRIEF DESCRIPTION OF THE DRAWINGS

The detailed description is described with reference to the accompanying figures. Entities represented in the figures may be indicative of one or more entities and thus reference may be made interchangeably to single or plural forms of the entities in the discussion.

DETAILED DESCRIPTION

Overview

Figure 1:
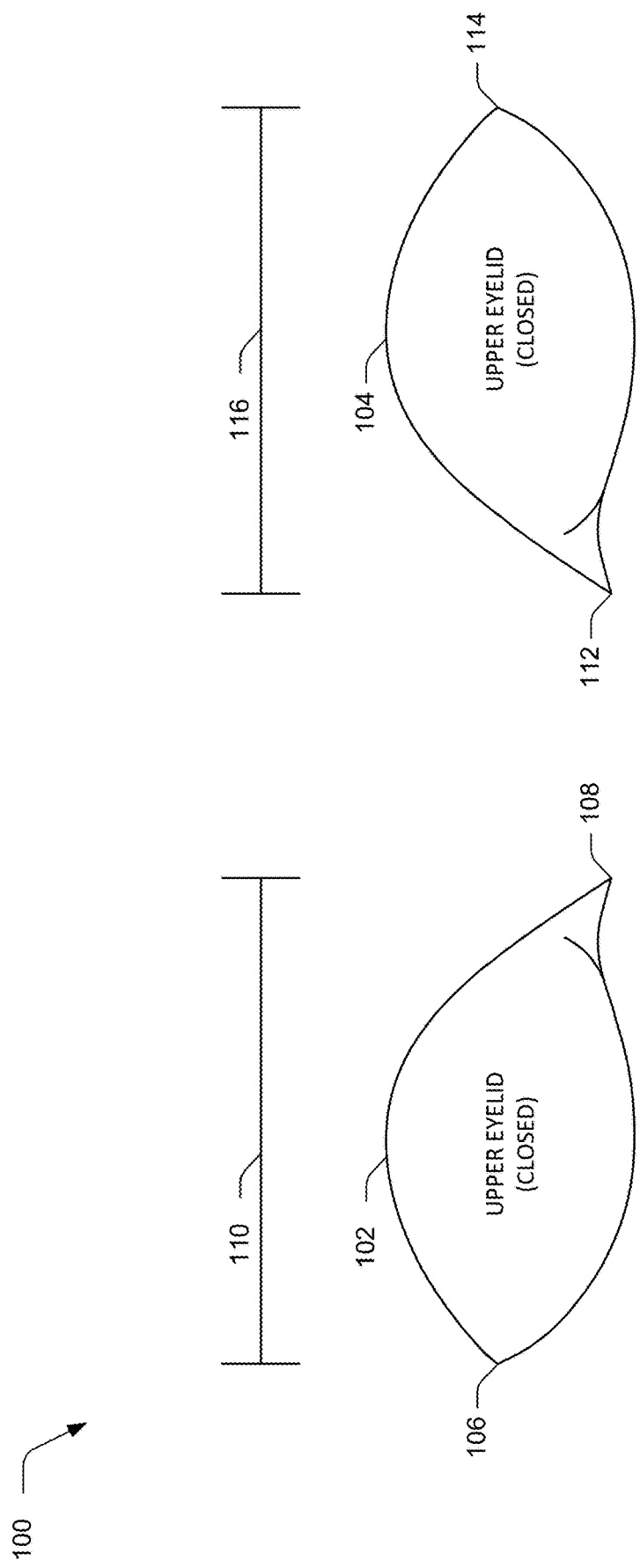
FIG. 1 is an illustration of an example representation of determining palpebral fissure width.

Dry eye syndrome adversely affects the lives of hundreds of millions of people globally which includes an estimated 15-25 million people in the US. The most widely used technique for treatment of dry eye in the US based on revenue is a prescription eye drop (cyclosporine ophthalmic emulsion 0.05%; Restasis) which increases tear production in about 15 percent of patients studied clinically. The same clinical study found that around 5 percent of patients given a placebo also increased tear production. Accordingly, conventional systems and techniques for managing dry eye syndrome are only marginally effective relative to placebos. Moreover, side effects of these conventional prescription eye drops include eye discomfort as well as itching and temporarily blurred vision.

Systems and techniques are described for management of dry eye syndrome which objectively demonstrate several improvements compared to conventional techniques for managing dry eye. In one example, a palpebral fissure width is determined as a distance between a medial canthus and a lateral canthus of closed eyelids. The medial canthus is the meeting point of the upper and lower eyelids closest to the nose while the lateral canthus is the meeting point of the eyelids closest to the ears. An ideal eyelash length is generated based on the distance. In one example, the ideal eyelash length may be generated as approximately one-third of the distance between the medial canthus and the lateral canthus of the closed eyelids.

Eyelashes of an upper eyelid of the closed eyelids are segmented into regions. For example, the eyelashes may be segmented into first, second, and third regions such that the first region is disposed between the second region and the third region. A prosthesis having the ideal eyelash length is attached to a candidate eyelash of the first region. A second prosthesis having a length that is less than the ideal eyelash length is attached to a candidate eyelash of the second region. A third prosthesis having a length that is greater than the ideal eyelash length is attached to a candidate eyelash of the third region.

The prostheses introduce multiple turbulences to airflow that is incident to a tear film. These turbulences disrupt the airflow and prevent the airflow from evaporating the tear film. By preventing the tear film from evaporating in this way, dry eye syndrome is managed safely and effectively. Clinical evaluations of the described systems for management of dry eye syndrome establish that the described systems are more effective at treating dry eye than conventional techniques. The described systems also do not include side effects such as those associated with conventional prescription eye drops. Further, patients treated using the described systems demonstrate a greater improvement in visual acuity than patients treated using conventional systems.

The ideal eyelash length can also be used for screening patients and identifying patients having eyelash lengths indicative of dry eye syndrome. In one example, a computing device implements an evaluation system to process a digital image depicting closed eyelids having eyelashes. The digital image can be captured using an image capture device of the computing device in an example. The evaluation system generates an indication for dry eye syndrome based on eyelash lengths of the eyelashes depicted in the digital image. The indication for dry eye syndrome is rendered in a user interface which also includes user interface elements enabling functionality associated with the indication for dry eye syndrome such as to generate a prescription for prostheses based on the palpebral fissure width and subsequently calculated eyelash lengths.

For example, the prescription may correspond to a particular type of dry eye management kit of several available types of dry eye management kits. In some examples, each type of dry eye management kit may include prostheses having lengths corresponding to a particular ideal eyelash length. The prostheses included in each dry eye management kit may be sterile as having been sterilized by ethylene oxide sterilization, gamma sterilization, etc. For example, each type of dry eye management kit may also include accessories such as applicators which are also designed for use with the particular ideal eyelash length.

In the following discussion, an example environment is first described that may employ the techniques described herein. Example procedures are also described which may be performed in the example environment as well as other environments. Consequently, performance of the example procedures is not limited to the example environment and the example environment is not limited to performance of the example procedures.

Examples of Dry Eye Syndrome Management

FIG. 1 is an illustration of an example representation 100 of determining palpebral fissure width. As shown, the representation 100 includes a right eye 102 and a left eye 104. The right eye 102 is illustrated as having closed eyelids with a right upper eyelid shown. The right eye 102 includes a lateral canthus 106 and a medial canthus 108 and a palpebral fissure width is determined as a distance 110 between the lateral canthus 106 and the medial canthus 108. The distance 110 can be determined using any suitable technique, e.g., the distance 110 may be measured using a pair of calipers, a ruler, a reticle, etc.

The left eye 104 is also illustrated as having closed eyelids, and a left upper eyelid is shown. The left eye 104 includes a medial canthus 112 and a lateral canthus 114. A palpebral fissure width for the left eye 104 is determined as a distance 116 between the medial canthus 112 and the lateral canthus 114. The distance 116 can be determined using any suitable technique, e.g., the distance 116 may be measured using a laser distance meter, a calibrated measuring chart, an optical overlay, etc.

The distances 110, 116 can be used to generate an ideal eyelash length. In one example, the ideal eyelash length may be expressed as:

$$L_{IDL} = D_{PFW} * \rho$$

where: $L_{IDL}$ is the ideal eyelash length; $D_{PFW}$ is the distance between the medial and lateral canthi; and p is a constant that is greater than zero.

For example, ρ is a constant between zero and one. In some examples, ρ may be a constant in a range of 0.20 to 0.45, e.g., ρ may be a constant of 0.33. In other examples, ρ may be a constant of less than 0.20 or greater than 0.45. A value of ρ may be determined heuristically, statistically, analytically, etc. In one example, the value of ρ is based on anatomical data that describes eyelash lengths of multiple mammalian species. In another example, the value of ρ is based on clinical data describing eyelash lengths of groups of patients having dry eye syndrome as well as groups of patients that do not have dry eye syndrome.

Figure 2:
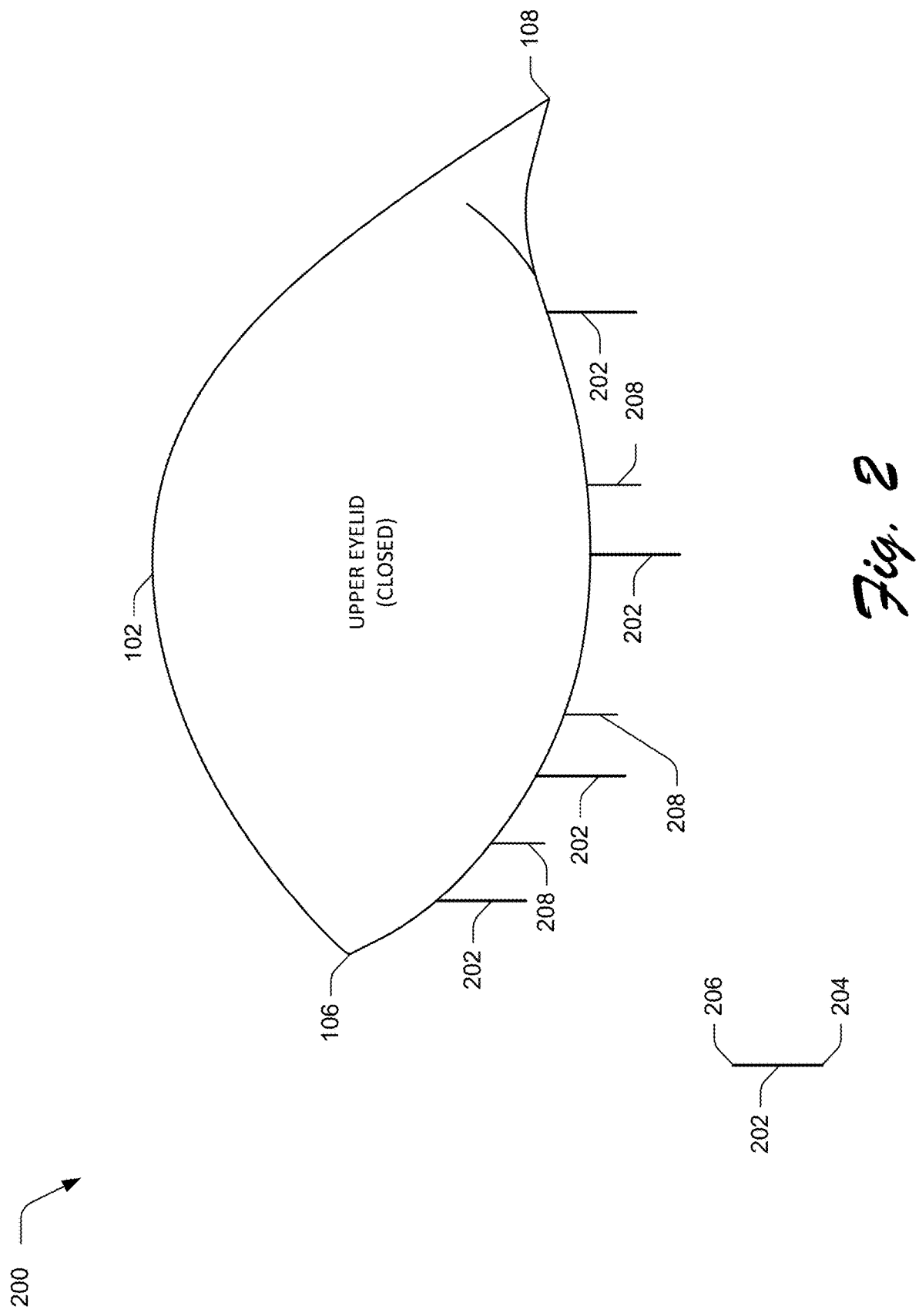
FIG. 2 is an illustration of an example representation of management of dry eye syndrome using prostheses having an ideal eyelash length.

FIG. 2 is an illustration of an example representation 200 of management of dry eye syndrome using prostheses having an ideal eyelash length. The representation 200 includes a prosthesis 202 having a prosthesis proximal end 204 and a prosthesis distal end 206. In the illustrated example, the prosthesis 202 has the ideal eyelash length based on the distance 110. In this example, the ideal eyelash length is an end-to-end measurement between the prosthesis proximal end 204 and the prosthesis distal end 206. For example, the ideal eyelash length is a total length between the prosthesis proximal end 204 and the prosthesis distal end 206.

Consider an example in which the distance 110 is approximately 33.0 millimeters and the value of ρ is 0.33. In this example, the ideal eyelash length is approximately 11.0 millimeters and the prosthesis has a length of 11.0 millimeters. Thus, the prosthesis proximal end 204 and the prosthesis distal end 206 are separated by 11.0 millimeters. Consider another example in which the distance 116 is approximately 30.0 millimeters and the value of ρ is 0.33. The ideal eyelash length is approximately 10.0 millimeters in this example.

In some examples, the prosthesis 202 has a width or a thickness in a range of 0.05 to 0.25 millimeters, e.g., the prosthesis 202 may have a width or thickness of approximately 0.15 millimeters. In other examples, the prosthesis 202 has a width or thickness of less than 0.05 millimeters or greater than 0.25 millimeters. In another example, the prosthesis 202 can have a width or thickness in a range of 0.01 to 0.5 millimeters. For example, the prosthesis 202 can have a geometry which has a variable width or thickness. In an example, the prosthesis 202 has a tapered geometry which decreases in width or thickness between the prosthesis distal end 206 and the prosthesis proximal end 204. For example, the prosthesis 202 can have a geometry which includes a curved portion such that the prosthesis 202 curves between the prosthesis distal end 206 and the prosthesis proximal end 204.

As illustrated in FIG. 2, several prostheses 202 are attached to the upper eyelid of the right eye 102. In some examples, the prostheses 202 are each attached to a candidate eyelash 208. The candidate eyelash 208 is a human eyelash and the prosthesis 202 can be attached to the candidate eyelash 208 by any suitable method. For example, an adhesive may be applied to the prosthesis distal end 206 and the adhesive can attach the prosthesis 202 to the candidate eyelash 208. As used herein, the term "adhesive" refers to glue, cement, mucilage, paste, or any other type of material configured to attach the prosthesis 202 to the candidate eyelash 208. In this manner, an adhesive joint attaches the prosthesis 202 to the candidate eyelash 208 in close proximity to the upper eyelid such that the prosthesis 202 overlays the candidate eyelash 208 and the prosthesis proximal end 204 extends past a proximal end of the candidate eyelash 208.

Although the prosthesis 202 is described as being attached to the candidate eyelash 208 by an adhesive such as a biocompatible adhesive, the prosthesis 202 can be attached to the candidate eyelash 208 using a crimp, a tie, a weld, an interference fit, etc. For example, the prosthesis 202 may have a geometry configured to facilitate attachment of the prosthesis 202 to the candidate eyelash 208 such as a channel having a channel width configured to house the candidate eyelash 208. In some examples, at least a portion of the prosthesis 202 can include an aperture and the candidate eyelash 208 may be disposed in the aperture. In one example, the prosthesis 202 includes a sleeve portion configured to envelop or cover a portion of the candidate eyelash 208. In another example, a portion of the prosthesis 202 may have a surface configured to increase an amount of surface area in contact between the prosthesis 202 and the candidate eyelash 208 such as a surface modified by a micro-abrasive process.

As shown in FIG. 2, four prostheses 202 are each attached to a candidate eyelash 208 and three additional candidate eyelashes 208 are available for attaching additional prostheses 202. In some examples, one prosthesis 202 is attached to each candidate eyelash 208 of the upper eyelid. In other examples, the prostheses 202 are attached to only a portion of the candidate eyelashes 208 of the upper eyelid as illustrated in FIG. 2. In some scenarios, one prosthesis 202 may be attached to multiple candidate eyelashes 208 such as to ensure that the one prosthesis 202 has adequate support.

The illustrated examples attach prostheses 202 to candidate eyelashes 208 of the upper eyelid; however, in some examples a prosthesis 202 may be attached to candidate eyelashes of a lower eyelid. In these examples, the prosthesis 202 would have a different length that corresponds to an ideal eyelash length for the lower eyelid. For example, the ideal eyelash length for the lower eyelid is less than the ideal eyelash length $L_{IDL}$.

Although the prosthesis 202 is described as being attached to the candidate eyelash 208, in some examples, the prosthesis 202 is attached directly to the upper eyelid. For example, the prostheses 202 may be attached directly to the upper eyelid by any suitable means such as an adhesive. In one example, the prostheses 202 are surgically implanted in the upper eyelid as a permanent or semi-permanent surgical implant.

Figure 3:
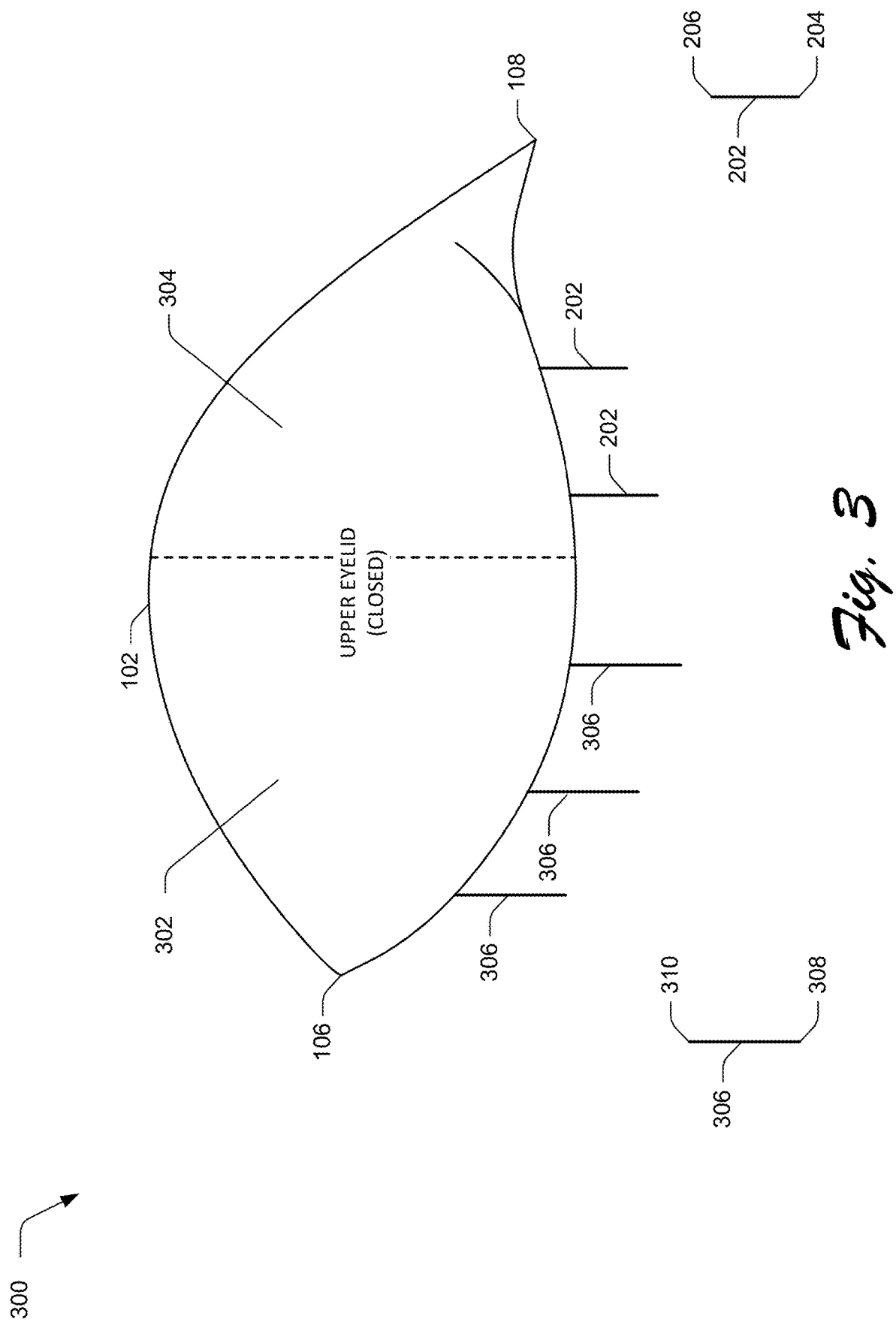
FIG. 3 is an illustration of an example representation of management of dry eye syndrome using first prostheses having an ideal eyelash length and second prostheses having a length greater than the ideal eyelash length.

FIG. 3 is an illustration of an example representation 300 of management of dry eye syndrome using first prostheses having an ideal eyelash length and second prostheses having a length greater than the ideal eyelash length. The representation 300 includes the upper eyelid of the right eye 102 which has been segmented into a first region 302 and a second region 304. In the illustrated example, the first region 302 includes a lateral portion of the upper eyelid and the second region 304 includes a medial portion of the upper eyelid. The representation 300 also includes the prosthesis 202 which has the ideal eyelash length and a longer prosthesis 306 which has a length that is greater than the ideal eyelash length. The longer prosthesis 306 has a proximal end 308 and a distal end 310.

As shown, the prostheses 202 are attached to candidate eyelashes 208 of the second region 304 while the longer prostheses 306 are attached to candidate eyelashes 208 of the first region 302. By attaching the longer prostheses 306 and the prostheses 202 to the candidate eyelashes 208 in this way, fluid dynamics of airflow is modified around the right eye 102. For example, this may introduce a turbulence which disrupts the airflow incident to a tear film of the right eye 102 which prevents the tear film from evaporating.

Figure 4:
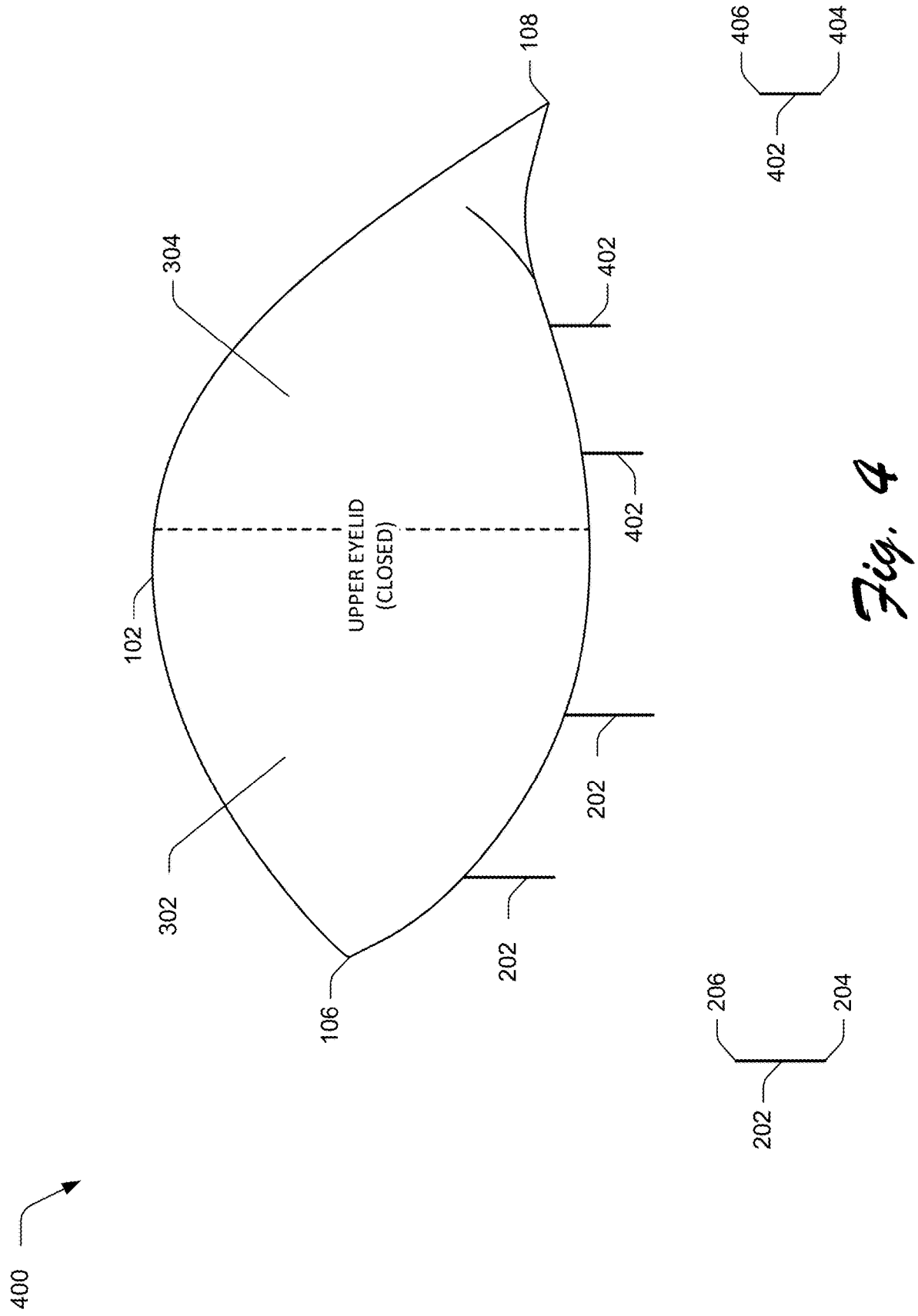
FIG. 4 is an illustration of an example representation of management of dry eye syndrome using first prostheses having an ideal eyelash length and second prostheses having a length less than the ideal eyelash length.

FIG. 4 is an illustration of an example representation 400 of management of dry eye syndrome using first prostheses having an ideal eyelash length and second prostheses having a length less than the ideal eyelash length. The representation 400 includes the upper eyelid of the right eye 102 which has been segmented into the first region 302 and the second region 304. In this example, the prostheses 202 having the ideal eyelash length are attached to candidate eyelashes 208 of the first region 302.

The representation 400 also includes a shorter prosthesis 402 which has a length that is less than the ideal eyelash length. The shorter prosthesis 402 has a proximal end 404 and a distal end 406. As shown, the shorter prostheses 402 are attached to candidate eyelashes 208 in the second region 304. By attaching the shorter prostheses 402 and the prostheses 202 to the candidate eyelashes 208 in this manner, a turbulence is introduced in the airflow around the right eye 102. This turbulence disrupts the airflow incident to the tear film of the right eye 102 which prevents the tear film from evaporating.

Figure 5:
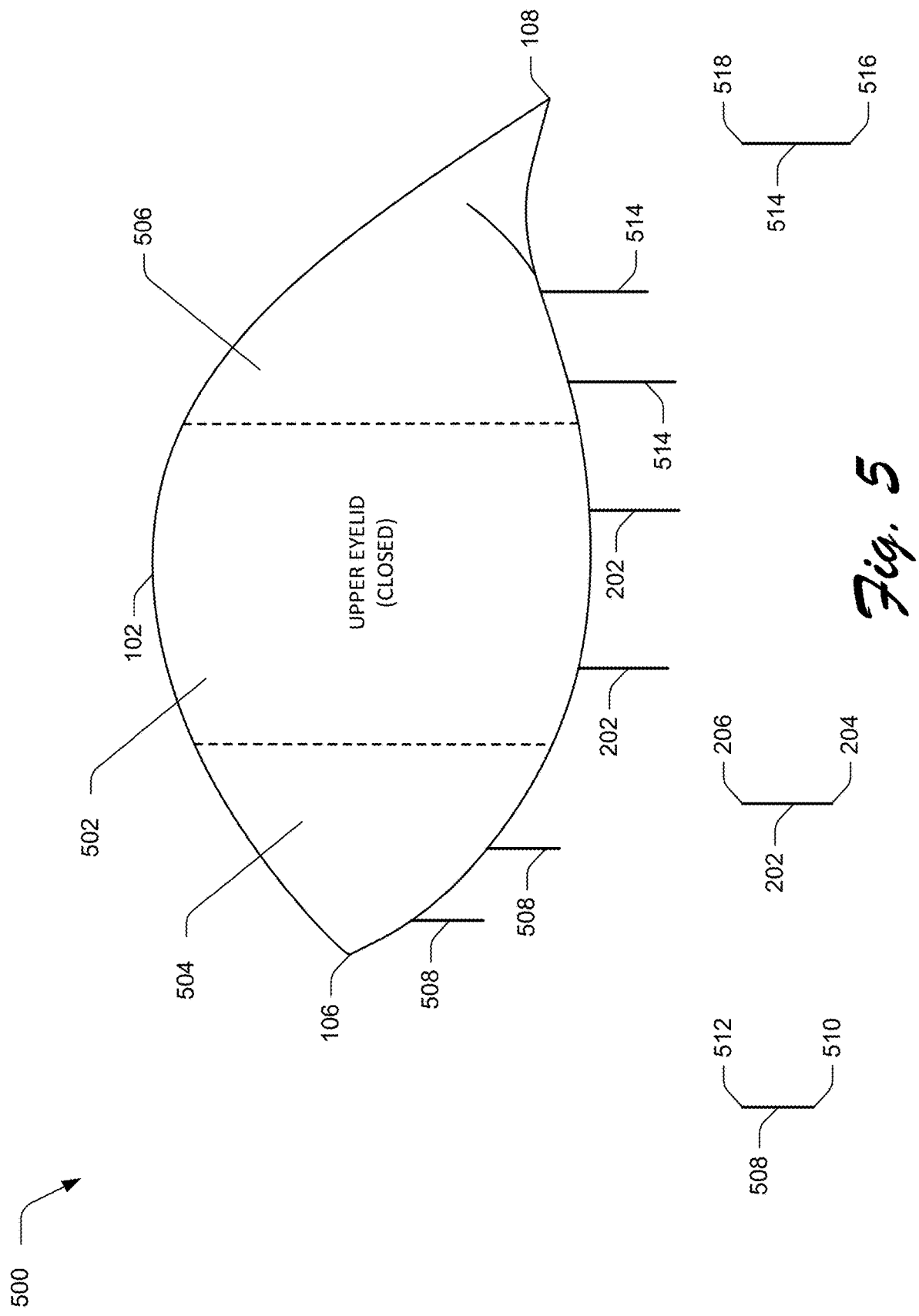
FIG. 5 is an illustration of an example representation of management of dry eye syndrome using first prostheses having an ideal eyelash length, second prostheses having a length less than the ideal eyelash length, and third prostheses having a length greater than the ideal eyelash length.

FIG. 5 is an illustration of an example representation 500 of management of dry eye syndrome using first prostheses having an ideal eyelash length, second prostheses having a length less than the ideal eyelash length, and third prostheses having a length greater than the ideal eyelash length. The representation 500 includes the upper eyelid of the right eye 102 which has been segmented into a first region 502, a second region 504, and a third region 506. As shown, the first region 502 is disposed between the second region 504 and the third region 506.

For example, the regions 502-506 may equally segment the upper eyelid such that each of the regions includes approximately an equal number of candidate eyelashes 208. In the illustrated example, the first region 502 includes approximately 40 percent of the candidate eyelashes 208 while the second region 504 and the third region 506 each include approximately 30 percent of the candidate eyelashes 208. Consider an example in which the upper eyelid of the right eye 102 includes approximately 120 candidate eyelashes 208. In this example, the first region 502 may include approximately 48 of the 120 candidate eyelashes 208, the second region 504 may include approximately 36 of 120 the candidate eyelashes 208, and the third region 506 may include approximately 36 of the 120 candidate eyelashes 208.

Consider another example in which the upper eyelid of the right eye 102 includes approximately 80 candidate eyelashes 208. In this example, the first region 502 may include approximately 42 of the 80 candidate eyelashes 208, the second region 504 may include approximately 24 of 80 the candidate eyelashes 208, and the third region 506 may include approximately 24 of the 80 candidate eyelashes 208. In other examples, the first region 502 may include a percentage of the candidate eyelashes 208 in a range of 25.0 to 65.0 percent, the second region 504 may include a percentage of the candidate eyelashes 208 in a range of 20.0 to 40.0 percent, and the third region 506 may include a percentage of the candidate eyelashes 208 in a range of 20.0 to 40.0 percent.

The representation 500 includes the prosthesis 202 having the ideal eyelash length. The representation 500 also includes a shorter prosthesis 508 having a proximal end 510 and a distal end 512 as well as a longer prosthesis 514 having a proximal end 516 and a distal end 518. The shorter prostheses 508 have lengths less than the ideal eyelash length while the longer prostheses 514 have lengths greater than the ideal eyelash length.

For example, the prostheses 202, the shorter prostheses 508, and the longer prostheses 514 may be included as part of a dry eye management kit. The dry eye management kit may be designed for a single-use and may include the prostheses 202, the shorter prostheses 508, and the longer prostheses 514 sterilized for use by ethylene oxide sterilization, gamma sterilization, etc. In some examples, the dry eye management kit may include devices designed for attaching the prostheses 202, the shorter prostheses 508, and the longer prostheses 514 to the candidate eyelashes 208.

The dry eye management kit may include a single-use instrument which includes a prostheses repository having the prostheses 202, the shorter prostheses 508, and the longer prostheses 514 oriented for attachment to the candidate eyelashes 208. For example, the single-use instrument and the prostheses 202, the shorter prostheses 508, and the longer prostheses 514 are sterilized for use by ethylene oxide sterilization, gamma sterilization, etc. In one example, the dry eye management kit can include a single-use forceps which may be used to remove a prosthesis 202, a shorter prosthesis 508, and/or a longer prosthesis 514 from the prostheses repository of the single-use instrument. This single-use forceps of the dry eye management kit may also be used to attach the prosthesis 202, the shorter prosthesis 508, and/or the longer prosthesis 514 to candidate eyelashes 208.

The dry eye management kit can include additional components as well. These additional components can be single-use and sterilized and may be usable to prepare candidate eyelashes 208 for prosthesis attachment and/or useable to attach the prosthesis 202, the shorter prosthesis 508, and/or the longer prosthesis 514 to candidate eyelashes 208. In some examples, the dry eye management kit can include sterile tape, sterile eyelash wipes, a tray or card, etc. In an example, the tray or card may be colored to create a visual color contrast between the tray or card and the prosthesis 202, the shorter prosthesis 508, and/or the longer prosthesis 514. In this example, the tray or card may be colored white to provide a contrast between prostheses having a dark color. For example, the dry eye management kit may be one of multiple dry eye management kits that each include the prostheses 202, the shorter prostheses 508, and the longer prostheses 514 having features unique to each dry eye management kit.

Consider an example in which each dry eye management kit of the multiple dry eye management kits is designed for use on an upper eyelid having a particular distance 110. In this example, a first dry eye management kit is designed for a first distance 110 and a second dry eye management kit is designed for a second distance 110. By way of example, the first dry eye management kit includes first prostheses 202 having a first ideal eyelash length based on the first distance 110, first shorter prostheses 508 having a length less than the first ideal eyelash length, and first longer prostheses 514 having a length greater than the first ideal eyelash length. Similarly, the second dry eye management kit includes second prostheses 202 having a second ideal eyelash length based on the second distance 110, second shorter prostheses 508 having a length less than the second ideal eyelash length, and second longer prostheses 514 having a length greater than the second ideal eyelash length.

In some examples, lengths of the shorter prostheses 508 and lengths of the longer prostheses 514 are a function of the ideal eyelash length which may be expressed as:

$$L_{sp} = L_{IDL} - \delta$$

$$L_{lp} = L_{IDL} + \delta$$

where: $L_{sp}$ is a length of the shorter prosthesis 508; $L_{lp}$ is a length of the longer prosthesis 514; and $\delta$ is a length constant.

Consider an example in which the distance 110 is approximately 33.0 millimeters, the value of $\rho$ is 0.33, and the value of $\delta$ is 1.0 millimeters. In this example, the prosthesis 202 has the ideal eyelash length of approximately 11.0 millimeters. For example, the shorter prosthesis 508 may have a length of approximately 10.0 millimeters and the longer prosthesis 514 may have a length of approximately 12.0 millimeters.

Consider an additional example in which the distance 110 is approximately 30.0 millimeters, the value of $\rho$ is 0.33, and the value of $\delta$ is 1.0 millimeters. In this additional example, the prosthesis 202 has the ideal eyelash length of approximately 10.0 millimeters. Thus, the shorter prosthesis 508 may have a length of approximately 9.0 millimeters and the longer prosthesis 514 may have a length of approximately 11.0 millimeters.

For example, the first dry eye management kit may be designed for a first distance 110 of approximately 33.0 millimeters and the second dry eye management kit may be designed for a second distance 110 of approximately 30.0 millimeters. The first dry eye management kit may include prostheses 202 having an ideal eyelash length of approximately 11.0 millimeters, shorter prostheses 508 having a length of approximately 10.0 millimeters, and longer prostheses 514 having a length of approximately 12.0 millimeters. The second dry eye management kit may include prostheses 202 having an ideal eyelash length of approximately 10.0 millimeters, shorter prostheses 508 having a length of approximately 9.0 millimeters, and longer prostheses 514 having a length of approximately 11.0 millimeters.

In one example, multiple prostheses 202 having the ideal eyelash length may be attached to candidate eyelashes 208 of the first region 502. For example, multiple shorter prostheses 508 can be attached to candidate eyelashes 208 of the second region 504 and multiple longer prostheses 514 may be attached to candidate eyelashes 208 of the third region 506. Consider an example in which prostheses 202, shorter prostheses 508, and longer prostheses 514 can be attached to candidate eyelashes 208 to blend lengths of the prostheses near junctions between the regions 502, 504, 506. In this example, a prosthesis 202 having the ideal eyelash length may be attached to a candidate eyelash 208 of the second region 504 near the junction between the first region 502 and the second region 504. Similarly, a prosthesis 202 having the ideal eyelash length may be attached to a candidate eyelash 208 of the third region 506 near the junction between the first region 502 and the third region 506.

Continuing the previous example, a shorter prosthesis 508 may be attached to a candidate eyelash 208 of the first region 502 near the junction between the first region 502 and the second region 504. For example, a longer prosthesis 514 can be attached to a candidate eyelash 208 of the first region 502 near the junction between the first region 502 and the third region 506. In this example, lengths of the prostheses are blended near junctions between the regions 502, 504, 506. For example, this may gradually transition lengths of prostheses attached to candidate eyelashes 208 near junctions between the regions 502, 504, 506.

As illustrated, the prostheses 202 are attached to candidate eyelashes 208 of the first region 502, the shorter prostheses 508 are attached to candidate eyelashes 208 of the second region 504, and the longer prostheses 514 are attached to candidate eyelashes 208 of the third region 506. Attaching the prostheses 202, the shorter prostheses 508, and the longer prostheses 514 to the candidate eyelashes 208 in this way introduces multiple turbulences to the airflow around the right eye 102. For example, movements of the candidate eyelashes 208 cause movements of the prostheses 202, the shorter prostheses 508, and/or the longer prostheses 514. The movements of the prostheses 202, the shorter prostheses 508, and/or the longer prostheses 514 introduce the multiple turbulences to the airflow around the right eye 102. These multiple turbulences disrupt the airflow incident to the tear film of the right eye 102 which prevents the airflow from evaporating the tear film. Thus, the tear film is maintained and dry eye syndrome is effectively managed for the right eye 102.

Although the introduction of the multiple turbulences to the airflow around the right eye 102 is effective to prevent the tear film from evaporating, there may be some limits to the clinically beneficial effects of introduction of these turbulences to the airflow. This is because introduction of too much turbulence to the airflow around the right eye 102 can damage a lipid layer of the tear film. The lipid layer prevents an underlying aqueous/mucin region of the tear film from evaporating and as a result, damaging the lipid layer can facilitate evaporation of the tear film. For this reason, lengths of the prostheses 202, the shorter prostheses 508, and the longer prostheses 514 introduce enough turbulence to the airflow incident to the tear film to prevent the tear film from evaporating but do not introduce turbulence sufficient to damage the lipid layer.

Figure 6:
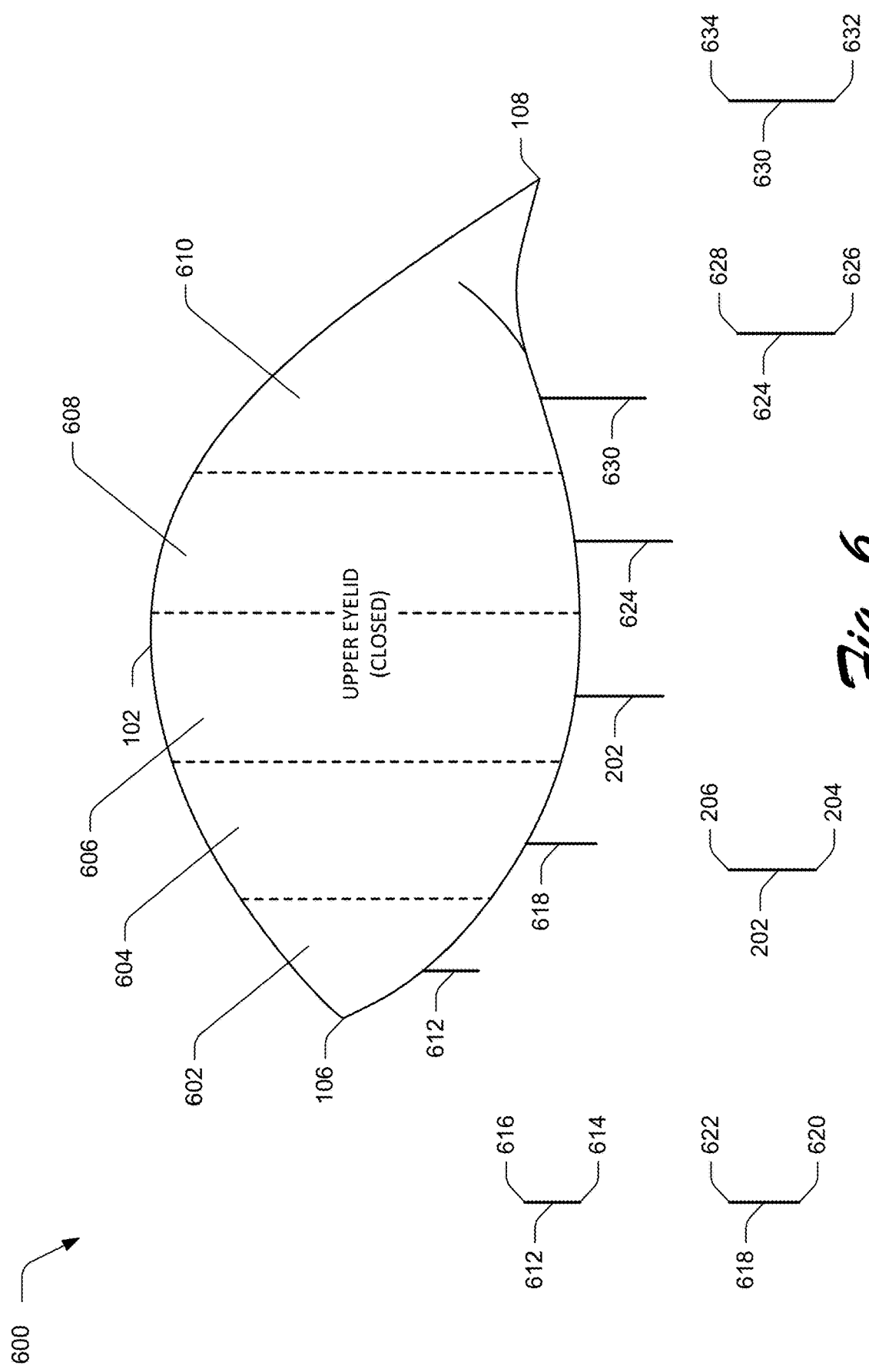
FIG. 6 is an illustration of an example representation of management of dry eye syndrome using prostheses having multiple different lengths.

FIG. 6 is an illustration of an example representation 600 of management of dry eye syndrome using prostheses having multiple different lengths. The representation 600 includes the right eye 102 which is segmented into a first region 602, a second region 604, a third region 606, a fourth region 608, and a fifth region 610. The regions 602-610 are illustrated as including various percentages of the candidate eyelashes 208; however, in some examples the regions 602-610 may include equal percentages of the candidate eyelashes 208.

The representation 600 includes the prosthesis 202 having the ideal eyelash length. The representation 600 also includes a first prosthesis 612 having a proximal end 614 and a distal end 616, a second prosthesis 618 having a proximal end 620 and a distal end 622, a third prosthesis 624 having a proximal end 626 and a distal end 628, and a fourth prosthesis 630 having a proximal end 632 and a distal end 634. As shown, each of the prosthesis 612-630 has a unique length such that a length of the first prosthesis 612 is less than a length of the second prosthesis 618 which is less than the ideal eyelash length of the prosthesis 202. For example, a length of the third prosthesis 624 is greater than the ideal eyelash length and a length of the fourth prosthesis 630 is greater than the length of the third prosthesis 624.

Consider an example in which the distance 110 is approximately 30.0 millimeters and the value of $\rho$ is 0.33. The ideal eyelash length is equal to a length of the prosthesis 202 which is approximately 10.0 millimeters. Continuing this example, the first prosthesis 612 may have a length of approximately 9.0 millimeters, the second prosthesis 618 can have a length of approximately 9.5 millimeters, the third prosthesis 624 may have a length of approximately 10.5 millimeters, and the fourth prosthesis 630 can have a length of approximately 11.0 millimeters.

Consider another example in which the distance 110 is approximately 33.0 millimeters and the value of ρ is 0.33. In this example, the ideal eyelash length is equal to a length of the prosthesis 202 which is approximately 11.0 millimeters. The first prosthesis 612 may have a length of approximately 8.0 millimeters, the second prosthesis 618 can have a length of approximately 9.0 millimeters, the third prosthesis 624 may have a length of approximately 12.0 millimeters, and the fourth prosthesis 630 can have a length of approximately 13.0 millimeters.

As illustrated in FIG. 6, the first prosthesis 612 is attached to a candidate eyelash 208 of the first region 602, the second prosthesis 618 is attached to a candidate eyelash 208 of the second region 604, the prosthesis 202 is attached to a candidate eyelash 208 of the third region 606, the third prosthesis 624 is attached to a candidate eyelash 208 of the fourth region 608, and the fourth prosthesis 630 is attached to a candidate eyelash 208 of the fifth region 610. Attaching the prosthesis 202 and the prostheses 612-630 to the candidate eyelashes 208 in this manner introduces multiple turbulences to the airflow around the right eye 102. These multiple turbulences disrupt the airflow incident to the tear film of the right eye 102 which prevents the tear film from evaporating. Accordingly, the tear film is maintained and dry eye syndrome is effectively managed for the right eye 102.

Figure 7:
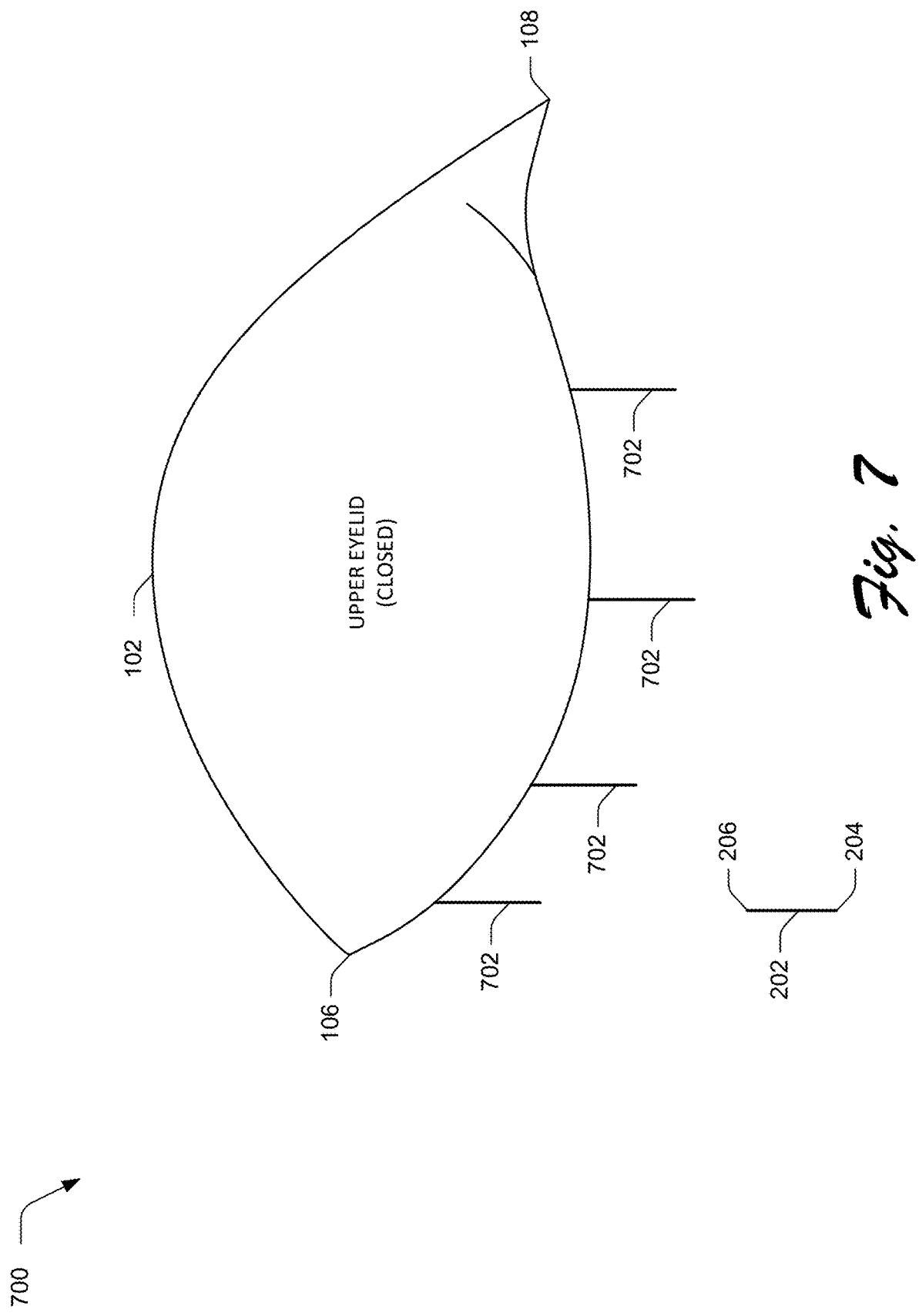
FIG. 7 is an illustration of an example representation of use of an ideal eyelash length to identify a patient with healthy tear film.

FIG. 7 is an illustration of an example representation 700 of use of an ideal eyelash length to identify a patient with healthy tear film. The representation 700 includes the right eye 102 and the prosthesis 202 which has the ideal eyelash length determined based on the distance 110. As shown, the representation 700 also includes eyelashes 702. A length of the eyelashes 702 is compared to the length of the prosthesis 202, e.g., the length of the eyelashes 702 can be visually compared to the length of the prosthesis 202. In this example, the length of the eyelashes 702 is greater than or equal to the length of the prosthesis 202. Thus, the length of the eyelashes 702 is greater than or equal to the ideal eyelash length. As a result, the right eye 102 has healthy tear film in this example and the right eye 102 is not a dry eye.

In some examples, a comparison between the length of the eyelashes 702 and the length of the prosthesis 202 is determinative as to whether the right eye 102 has dry eye syndrome or whether the right eye 102 does not have dry eye syndrome. In other examples, the comparison between the length of the eyelashes 702 and the length of the prosthesis 202 is used as a screening for performing additional testing. For example, the presence or absence of dry eye syndrome may be confirmed by conducting an additional test such as a survey, a Schirmer's test, a slit lamp test, a tear break up time test, a tear meniscus height test, etc.

Figure 8:
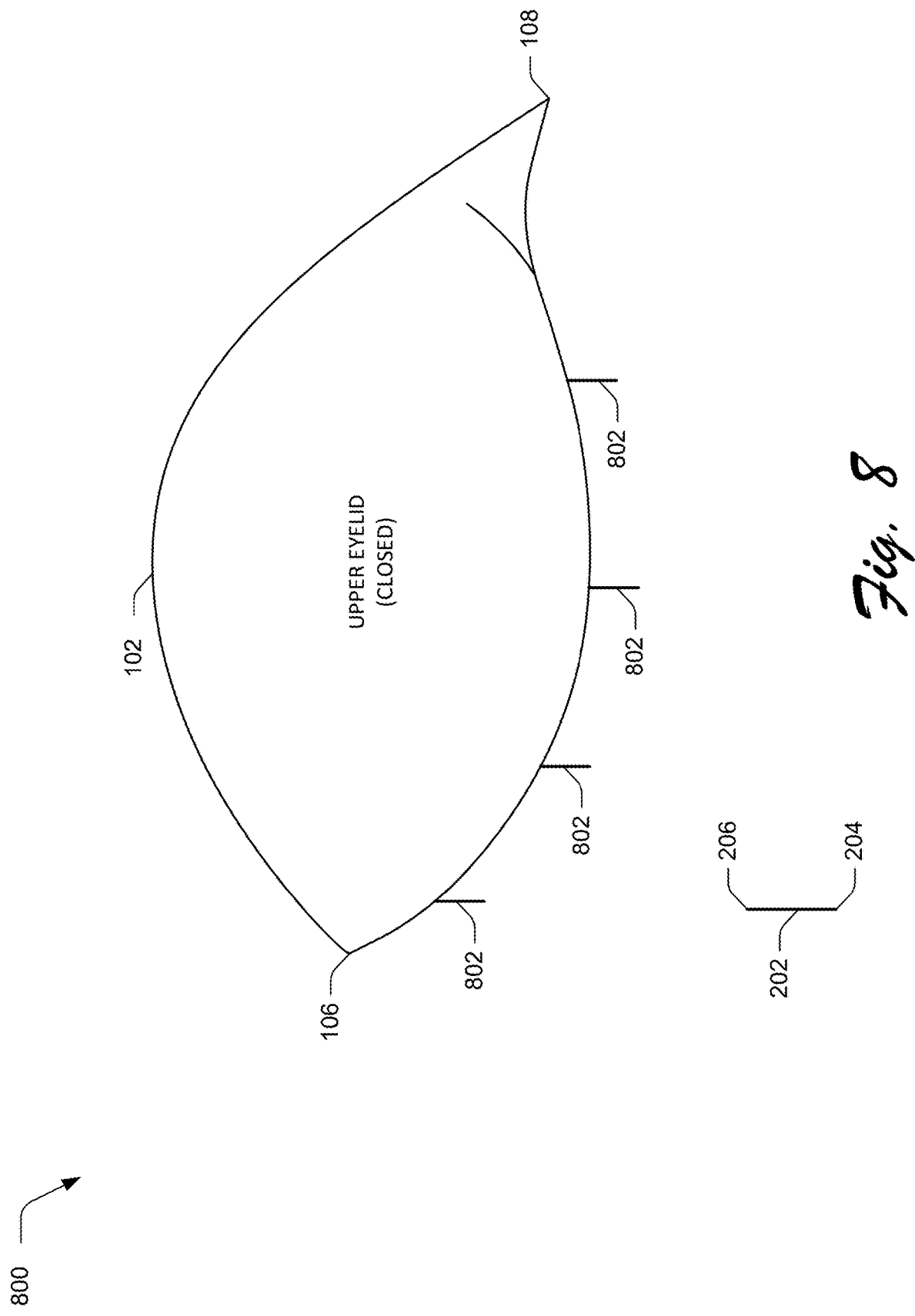
FIG. 8 is an illustration of an example representation of use of an ideal eyelash length to identify a patient with dry eye syndrome.

FIG. 8 is an illustration of an example representation 800 of use of an ideal eyelash length to identify a patient with dry eye syndrome. The representation 800 includes the right eye 102 and the prosthesis 202 which has the ideal eyelash length. As shown, the representation 800 includes eyelashes 802. A length of the eyelashes 802 is compared (e.g., visually compared) to a length of the prosthesis 202. In this example, the eyelashes 802 are not longer than the prosthesis 202. The eyelashes 802 are also not as long as the prosthesis 202. As illustrated, the eyelashes 802 are shorter than the prosthesis 202. Accordingly, the eyelashes 802 are shorter than the ideal eyelash length. As a result, the right eye 102 has dry eye syndrome. This comparison can be determinative as diagnosing the right eye 102 as having dry eye syndrome or the comparison can be used as part of screening to indicate whether an additional test for dry eye syndrome should be performed.

Figure 9:
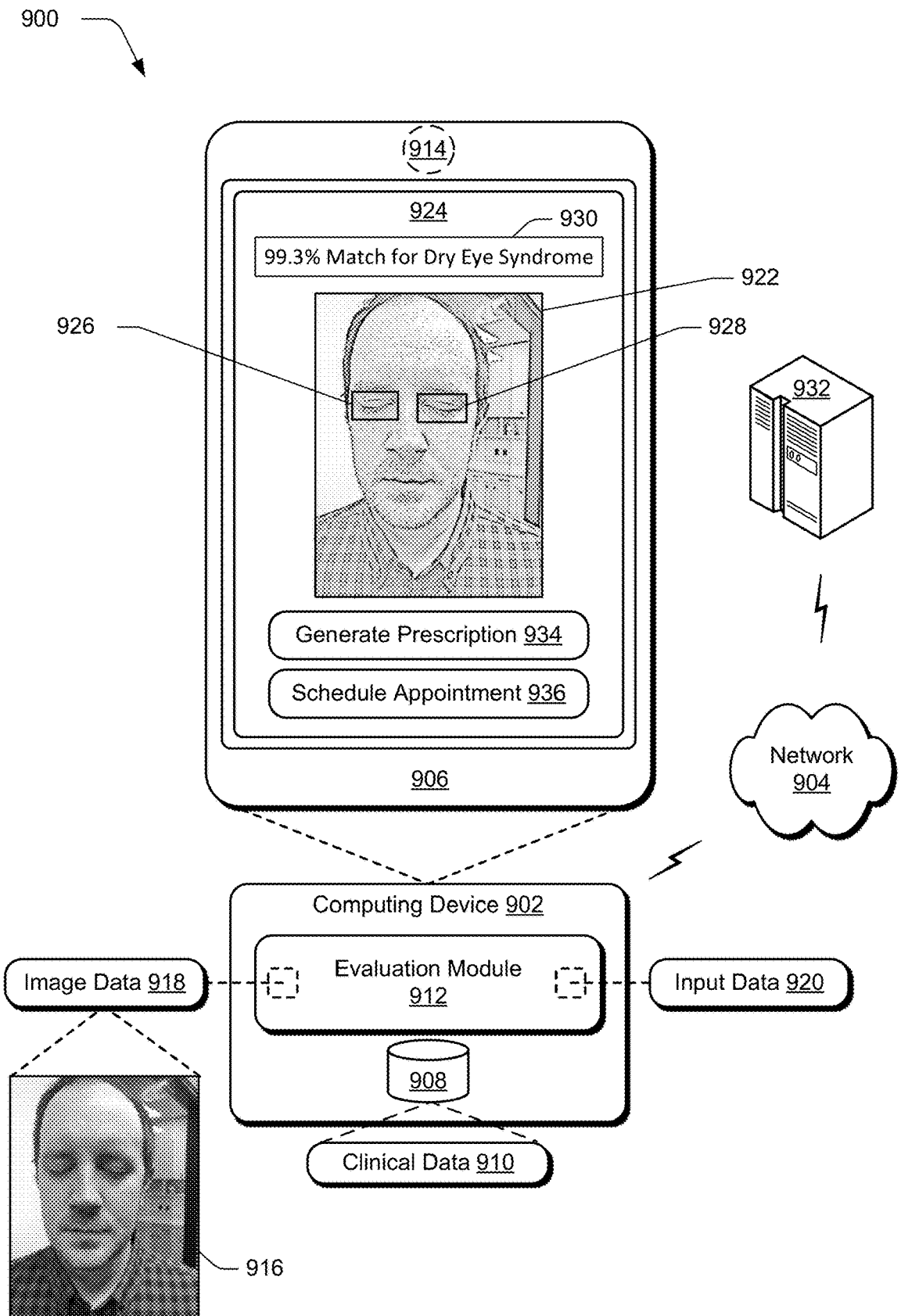
FIG. 9 is an illustration of an environment in an example implementation that is operable to employ systems and techniques as described herein.

FIG. 9 is an illustration of an environment 900 in an example implementation that is operable to employ systems and techniques as described herein. The illustrated environment 900 includes a computing device 902 connected to a network 904. The computing device 902 may be configured as a desktop computer, a laptop computer, a mobile device (e.g., assuming a handheld configuration such as a tablet or mobile phone), and so forth. Thus, the computing device 902 may range from a full resource device with substantial memory and processor resources (e.g., personal computers, game consoles) to a low-resource device with limited memory and/or processing resources (e.g., mobile devices). Additionally, the computing device 902 may be representative of a plurality of different devices, such as multiple servers utilized by a business to perform operations "over the cloud."

The illustrated environment 900 also includes a display device 906. A variety of device configurations may be used to implement the computing device 902 and/or the display device 906. The computing device 902 includes a storage device 908 which is illustrated to include clinical data 910. For example, the clinical data 910 generally describes aspects of dry eye syndrome and eyelash length which includes information correlating a likelihood of having dry eye syndrome to particular eyelash lengths.

The computing device 902 also includes an evaluation module 912 that implements the techniques and features as described herein. The computing device 902 and/or the display device 906 includes an image capture device 914 such as a digital camera. In some examples, the image capture device 914 may be included as part of the computing device 902 such as in examples in which the computing device 902 is configured as a mobile device. In the illustrated example, the computing device 902 is a mobile device (e.g., a smartphone) and the image capture device 914 is a digital camera of the mobile device. In other examples, the image capture device 914 may be communicatively coupled to the computing device 902 via a wireless or a wired connection.

The image capture device 914 can be implemented to capture a digital image 916 which is illustrated to be included in image data 918. As shown, the digital image 916 depicts a person having closed eyelids in this example. The evaluation module 912 is illustrated as having, receiving, and/or transmitting the image data 918 and input data 920. The input data 920 describes optional information about the person depicted in the digital image 916. For example, the input data 920 may describe information including the person's age, the person's gender, medications the person currently takes, whether or not the person wears contact lenses, etc.

In one example, the computing device 902 may implement the evaluation module 912 to receive the image data 918 and the optional input data 920, and the evaluation module 912 processes the image data 918, the optional input data 920, and/or the clinical data 910. As part of this processing, the evaluation module 912 detects objects depicted in the digital image 916 which is illustrated as a feature map 922 rendered in a user interface 924 of the display device 906.

The evaluation module 912 processes the image data 918 and identifies the person's right eye 102 and the person's left eye 104 which are enclosed within bounding boxes 926 and 928, respectively. The evaluation module 912 determines the distance 110 and the distance 116 and generates an ideal eyelash length corresponding to the right eye 102 and an ideal eyelash length corresponding to the left eye 104. The evaluation module 912 compares the generated ideal eyelash lengths to the person's eyelashes depicted in the digital image 916 to generate an indication 930 of dry eye syndrome which is rendered in the user interface 924. In the illustrated example, the indication 930 is rendered as text communicating a "99.3% Match for Dry Eye Syndrome."

The evaluation module 912 communicates the indication 930 to a dry eye service 932 via the network 904. The dry eye service 932 receives the indication 930 and communicates data to the evaluation module 912 via the network 904. The evaluation module 912 receives this data and processes the data to generate user interface elements 934 and 936 which are rendered in the user interface 924. A user, e.g., the person depicted in the digital image 916, can interact with user interface element 934 to generate a prescription and/or interact with user interface element 936 to schedule an appointment. For example, the user can select user interface elements 934, 936 by providing a user input in the user interface 924 such as touch input in an example in which the user interface 924 includes a touchscreen.

Figure 10:
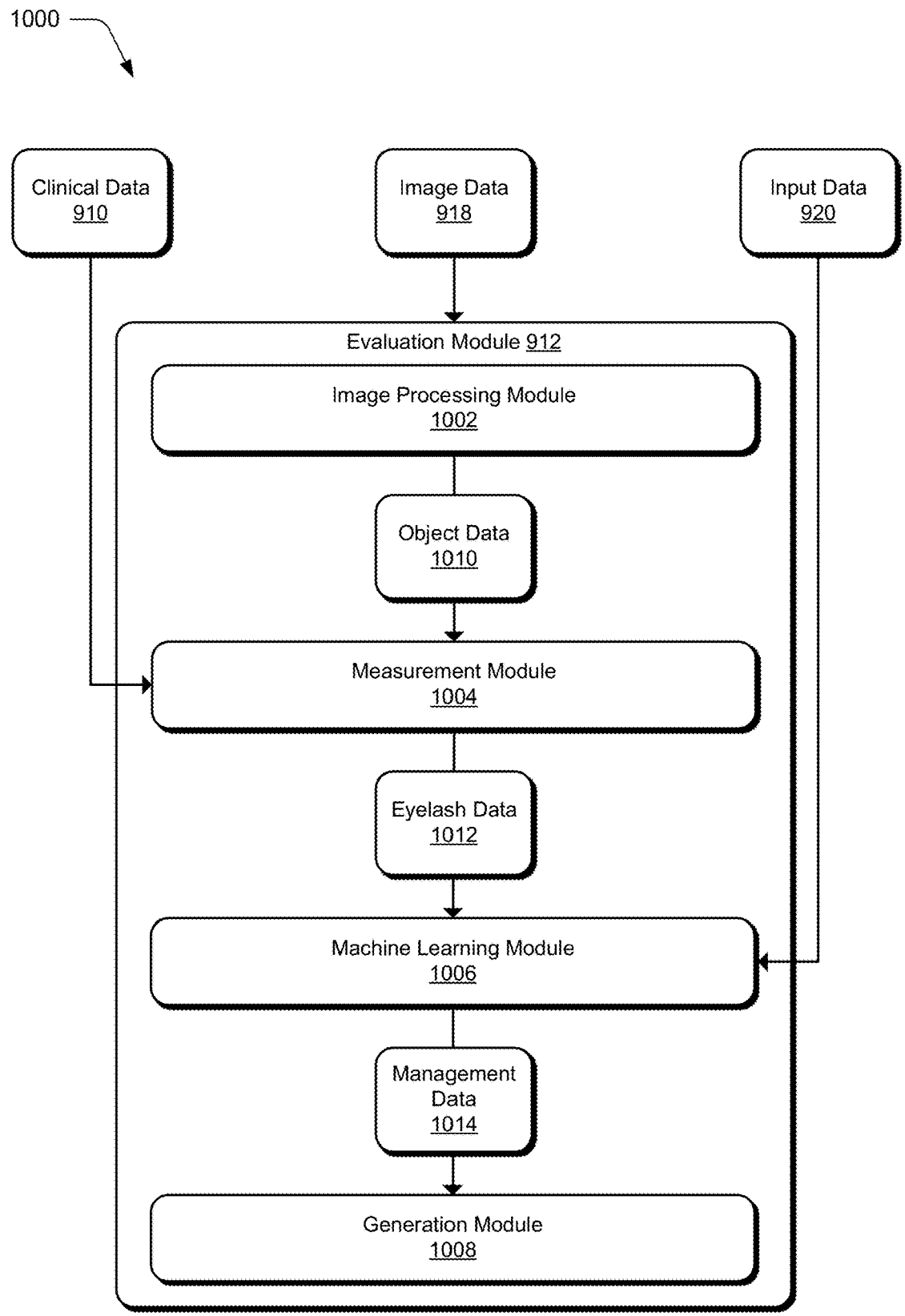
FIG. 10 depicts a system in an example implementation showing operation of an evaluation module.

FIG. 10 depicts a system 1000 in an example implementation showing operation of an evaluation module 912. The evaluation module 912 is illustrated to include an image processing module 1002, a measurement module 1004, a machine learning module 1006, and a generation module 1008. As illustrated, the image processing module 1002 receives the image data 918 and processes the image data to generate object data 1010. For example, the image processing module 1002 processes the image data 918 to detect objects depicted in the digital image 916. The image processing module 1002 then identifies each object detected in the digital image 916 and generates the object data 1010 as describing the identified objects.

The measurement module 1004 receives the object data 1010 and the clinical data 910. For example, the measurement module 1004 processes the object data 1010 and the clinical data 910 to generate eyelash data 1012. As shown, the measurement module 1004 processes the object data 1010 and identifies the right eye 102 and the left eye 104. The measurement module 1004 then determines the distance 110 for the right eye 102 and the distance 116 for the left eye 104 which the measurement module 1004 uses to determine an ideal eyelash length for the right eye 102 and an ideal eyelash length for the left eye 104.

The measurement module 1004 compares these ideal eyelash lengths with each eyelash depicted in the digital image 916. Finally, the measurement module 1004 generates the eyelash data 1012 as describing each of the comparisons. In some examples, it may be unnecessary for the measurement module to compare the ideal eyelash length generated for the right eye 102 with every eyelash of the right eye 102 or to compare the ideal eyelash length generated for the left eye 104 with every eyelash of the left eye 104. In these examples, the measurement module 1004 may generate the eyelash data 1012 as describing comparisons between ideal eyelash lengths and eyelashes for a portion of the eyelashes depicted in the digital image 916.

The machine learning module 1006 receives the eyelash data 1012 and the optional input data 920. The machine learning module 1006 includes a machine learning model. As used herein, the term "machine learning model" refers to a computer representation that can be tuned (e.g., trained) based on inputs to approximate unknown functions. In particular, the term "machine learning model" can include a model that utilizes algorithms to learn from, and make predictions on, known data by analyzing the known data to learn to generate outputs that reflect patterns and attributes of the known data. According to various implementations, such a machine learning model uses supervised learning, semi-supervised learning, unsupervised learning, or reinforcement learning. For example, the machine learning model can include, but is not limited to, clustering, decision trees, support vector machines, linear regression, logistic regression, Bayesian networks, random forest learning, dimensionality reduction algorithms, boosting algorithms, artificial neural networks (e.g., fully-connected neural networks, deep convolutional neural networks, or recurrent neural networks), deep learning, etc. Thus, a machine learning model makes high-level abstractions in data by generating data-driven predictions or decisions from the known input data.

The machine learning module 1006 processes the eyelash data 1012 as an input to the machine learning model. For example, the measurement module 1004 generates the eyelash data 1012 in a format suitable for processing as an input to the machine learning model. The machine learning model may include a region proposal network of a Faster R-Convolutional Neural Network (Faster R-CNN) using a convolutional neural network such as ResNet-101. The machine learning model is trained to generate indications of dry eye syndrome using training data. During training, a loss function is minimized such as an L1 or L2 loss function. Once trained, the machine learning model receives the eyelash data 1012 as an input and generates management data 1014.

The management data 1014 describes an indication of dry eye syndrome which can be an indication such as that dry eye is present or that dry eye is not present. The indication of dry eye syndrome may also be a probability which can be in terms of a likelihood that dry eye is present or in terms of a likelihood that dry eye is not present. The generating module 1008 receives the management data 1014 and processes the management data 1014, e.g., to render the indication 930 in the user interface 924.

In general, functionality, features, and concepts described in relation to the examples above and below may be employed in the context of the example procedures described in this section. Further, functionality, features, and concepts described in relation to different figures and examples in this document may be interchanged among one another and are not limited to implementation in the context of a particular figure or procedure. Moreover, blocks associated with different representative procedures and corresponding figures herein may be applied together and/or combined in different ways. Thus, individual functionality, features, and concepts described in relation to different example environments, devices, components, figures, and procedures herein may be used in any suitable combinations and are not limited to the particular combinations represented by the enumerated examples in this description.

Example Procedures

The following discussion describes techniques that may be implemented utilizing the previously described systems and devices. Aspects of each of the procedures may be implemented in hardware, firmware, software, or a combination thereof. The procedures are shown as a set of blocks that specify operations performed by one or more devices and are not necessarily limited to the orders shown for performing the operations by the respective blocks. In portions of the following discussion, reference may be made to FIGS. 1-10.

Figure 11:
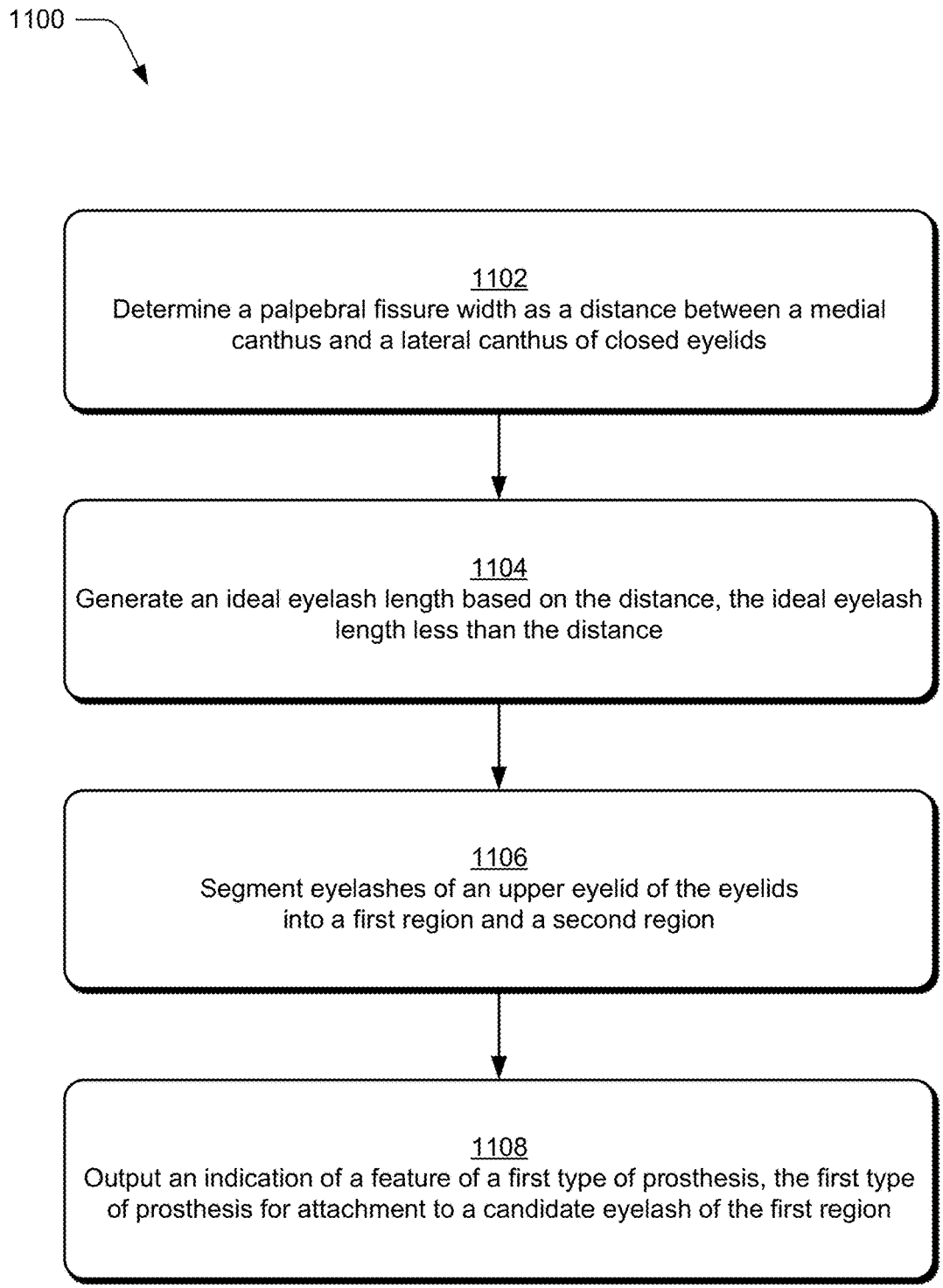
FIG. 11 is a flow diagram depicting a procedure in an example implementation in which an indication of a feature of a first type of prosthesis is output.

FIG. 11 is a flow diagram depicting a procedure 1100 in an example implementation in which an indication of a feature of a first type of prosthesis is output. A palpebral fissure width is determined as a distance between a medial canthus and a lateral canthus of closed eyelids (block 1102). For example, the computing device 902 can implement the evaluation module 912 to determine the palpebral fissure width as the distance. An ideal eyelash length is generated (block 1104) based on the distance, the ideal eyelash length less than the distance. In one example, the evaluation module 912 generates the ideal eyelash length.

Eyelashes of an upper eyelid of the eyelids are segmented into a first region and a second region (block 1106). For example, the evaluation module 912 may segment the eyelashes into the first region and the second region. An indication of a feature of a first type of prosthesis is output (block 1108), the first type of prosthesis for attachment to a candidate eyelash of the first region. The computing device 902 may implement the evaluation module 912 to output the indication of the feature of the first type of prosthesis.

Figure 12:
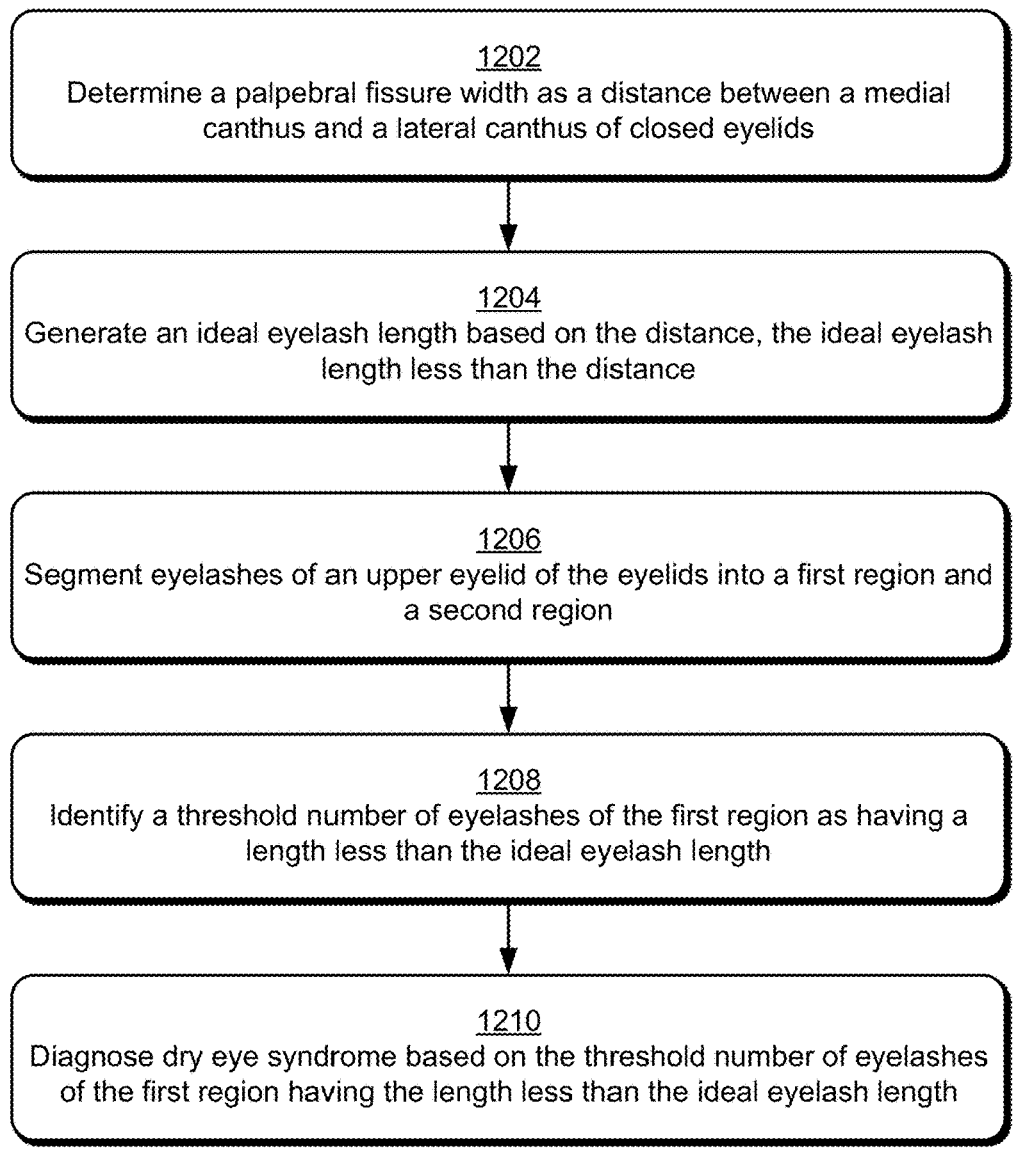
FIG. 12 is a flow diagram depicting a procedure in an example implementation in which dry eye syndrome is diagnosed based on a threshold number of eyelashes having a length less than an ideal eyelash length.

FIG. 12 is a flow diagram depicting a procedure 1200 in an example implementation in which dry eye syndrome is diagnosed based on a threshold number of eyelashes having a length less than an ideal eyelash length. A palpebral fissure width is determined as a distance between a medial canthus and a lateral canthus of closed eyelids (block 1202). The computing device 902 can implement the evaluation module 912 to determine the palpebral fissure width as the distance. An ideal eyelash length is generated (block 1204) based on the distance, the ideal eyelash length less than the distance. For example, the evaluation module 912 generates the ideal eyelash length.

Eyelashes of an upper eyelid of the eyelids are segmented into a first region and a second region (block 1206). In one example, the evaluation module 912 segments the eyelashes into the first region and the second region. A threshold number of eyelashes of the first region are identified as having a length less than the ideal eyelash length (block 1208). The evaluation module 912 identifies the threshold number of eyelashes of the first region as having less than the ideal eyelash length. Dry eye syndrome is diagnosed based on the threshold number of eyelashes of the first region having the length less than the ideal eyelash length (block 1210). For example, the evaluation module 912 diagnoses dry eye syndrome based on the threshold number of eyelashes of the first region having the length less than the ideal eyelash length.

Example System and Device

Figure 13:
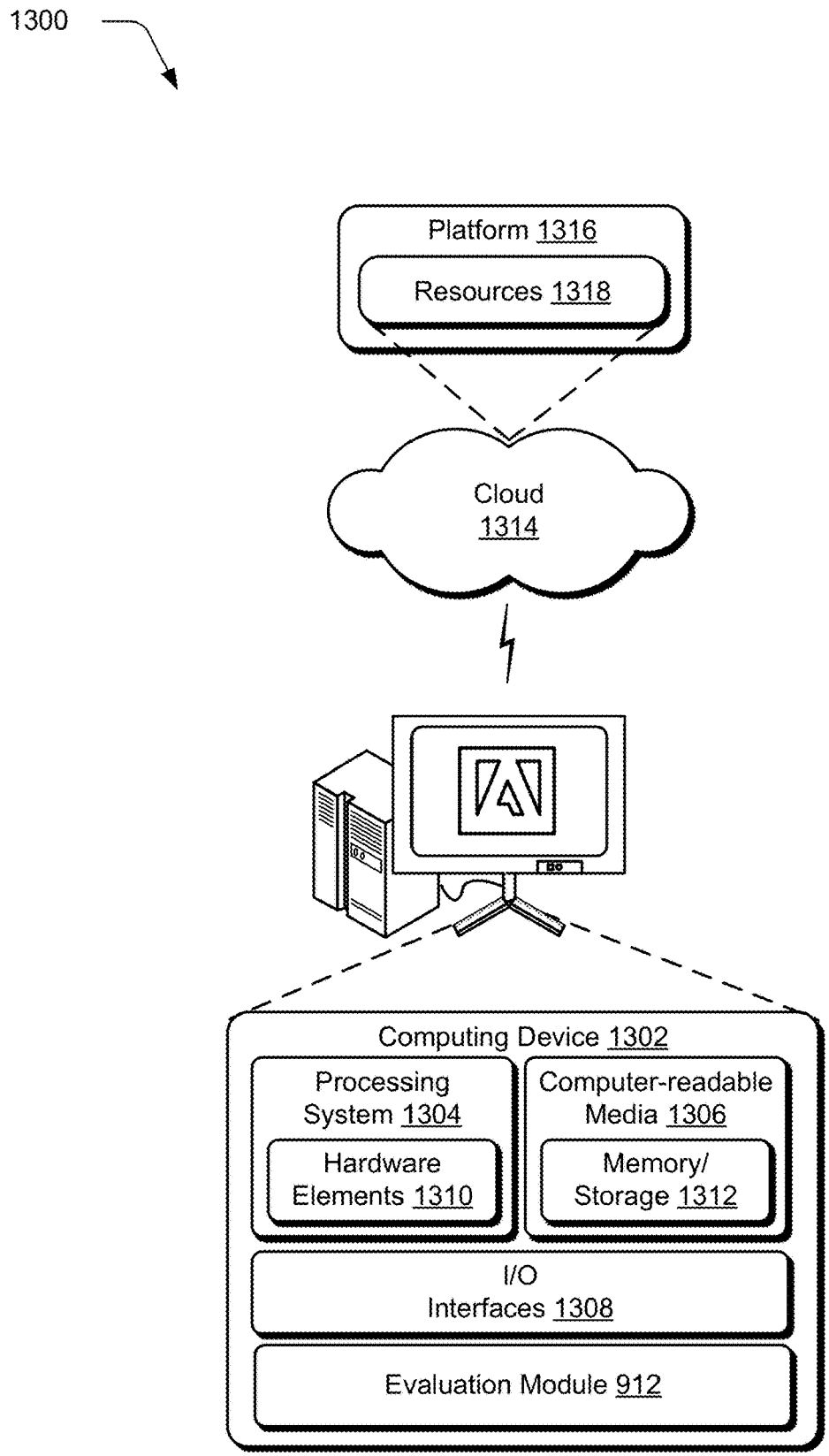
FIG. 13 illustrates an example system that includes an example computing device that is representative of one or more computing systems and/or devices that may implement the various techniques described herein.

FIG. 13 illustrates an example system 1300 that includes an example computing device that is representative of one or more computing systems and/or devices that may implement the various techniques described herein. This is illustrated through inclusion of the evaluation module 912. The computing device 1302 may be, for example, a server of a service provider, a device associated with a client (e.g., a client device), an on-chip system, and/or any other suitable computing device or computing system.

The example computing device 1302 as illustrated includes a processing system 1304, one or more computer-readable media 1306, and one or more I/O interfaces 1308 that are communicatively coupled, one to another. Although not shown, the computing device 1302 may further include a system bus or other data and command transfer system that couples the various components, one to another. A system bus can include any one or combination of different bus structures, such as a memory bus or memory controller, a peripheral bus, a universal serial bus, and/or a processor or local bus that utilizes any of a variety of bus architectures. A variety of other examples are also contemplated, such as control and data lines.

The processing system 1304 is representative of functionality to perform one or more operations using hardware. Accordingly, the processing system 1304 is illustrated as including hardware elements 1310 that may be configured as processors, functional blocks, and so forth. This may include implementation in hardware as an application specific integrated circuit or other logic device formed using one or more semiconductors. The hardware elements 1310 are not limited by the materials from which they are formed or the processing mechanisms employed therein. For example, processors may be comprised of semiconductor(s) and/or transistors (e.g., electronic integrated circuits (ICs)). In such a context, processor-executable instructions may be electronically-executable instructions.

The computer-readable media 1306 is illustrated as including a memory/storage component 1312. The memory/storage component represents memory/storage capacity associated with one or more computer-readable media. The memory/storage component 1312 may include volatile media (such as random access memory (RAM)) and/or nonvolatile media (such as read only memory (ROM), Flash memory, optical disks, magnetic disks, and so forth). The memory/storage component 1312 may include fixed media (e.g., RAM, ROM, a fixed hard drive, and so on) as well as removable media (e.g., Flash memory, a removable hard drive, an optical disc, and so forth). The computer-readable media 1306 may be configured in a variety of other ways as further described below.

Input/output interface(s) 1308 are representative of functionality to allow a user to enter commands and information to computing device 1302, and also allow information to be presented to the user and/or other components or devices using various input/output devices. Examples of input devices include a keyboard, a cursor control device (e.g., a mouse), a microphone, a scanner, touch functionality (e.g., capacitive or other sensors that are configured to detect physical touch), a camera (e.g., which may employ visible or non-visible wavelengths such as infrared frequencies to recognize movement as gestures that do not involve touch), and so forth. Examples of output devices include a display device (e.g., a monitor or projector), speakers, a printer, a network card, tactile-response device, and so forth. Thus, the computing device 1302 may be configured in a variety of ways as further described below to support user interaction.

Various techniques may be described herein in the general context of software, hardware elements, or program modules. Generally, such modules include routines, programs, objects, elements, components, data structures, and so forth that perform particular tasks or implement particular abstract data types. The terms "module," "functionality," and "component" as used herein generally represent software, firmware, hardware, or a combination thereof. The features of the techniques described herein are platform-independent, meaning that the techniques may be implemented on a variety of commercial computing platforms having a variety of processors.

An implementation of the described modules and techniques may be stored on or transmitted across some form of computer-readable media. The computer-readable media may include a variety of media that may be accessed by the computing device 1302. By way of example, and not limitation, computer-readable media may include "computer-readable storage media" and "computer-readable signal media."

"Computer-readable storage media" may refer to media and/or devices that enable persistent and/or non-transitory storage of information in contrast to mere signal transmission, carrier waves, or signals per se. Thus, computer-readable storage media refers to non-signal bearing media. The computer-readable storage media includes hardware such as volatile and non-volatile, removable and non-removable media and/or storage devices implemented in a method or technology suitable for storage of information such as computer readable instructions, data structures, program modules, logic elements/circuits, or other data. Examples of computer-readable storage media may include, but are not limited to, RAM, ROM, EEPROM, flash memory or other memory technology, CD-ROM, digital versatile disks (DVD) or other optical storage, hard disks, magnetic cassettes, magnetic tape, magnetic disk storage or other magnetic storage devices, or other storage device, tangible media, or article of manufacture suitable to store the desired information and which may be accessed by a computer.

"Computer-readable signal media" may refer to a signal-bearing medium that is configured to transmit instructions to the hardware of the computing device 1302, such as via a network. Signal media typically may embody computer readable instructions, data structures, program modules, or other data in a modulated data signal, such as carrier waves, data signals, or other transport mechanism. Signal media also include any information delivery media. The term "modulated data signal" means a signal that has one or more of its characteristics set or changed in such a manner as to encode information in the signal. By way of example, and not limitation, communication media include wired media such as a wired network or direct-wired connection, and wireless media such as acoustic, RF, infrared, and other wireless media.

As previously described, hardware elements 1310 and computer-readable media 1306 are representative of modules, programmable device logic and/or fixed device logic implemented in a hardware form that may be employed in some embodiments to implement at least some aspects of the techniques described herein, such as to perform one or more instructions. Hardware may include components of an integrated circuit or on-chip system, an application-specific integrated circuit (ASIC), a field-programmable gate array (FPGA), a complex programmable logic device (CPLD), and other implementations in silicon or other hardware. In this context, hardware may operate as a processing device that performs program tasks defined by instructions and/or logic embodied by the hardware as well as a hardware utilized to store instructions for execution, e.g., the computer-readable storage media described previously.

Combinations of the foregoing may also be employed to implement various techniques described herein. Accordingly, software, hardware, or executable modules may be implemented as one or more instructions and/or logic embodied on some form of computer-readable storage media and/or by one or more hardware elements 1310. The computing device 1302 may be configured to implement particular instructions and/or functions corresponding to the software and/or hardware modules. Accordingly, implementation of a module that is executable by the computing device 1302 as software may be achieved at least partially in hardware, e.g., through use of computer-readable storage media and/or hardware elements 1310 of the processing system 1304. The instructions and/or functions may be executable/operable by one or more articles of manufacture (for example, one or more computing devices 1302 and/or processing systems 1304) to implement techniques, modules, and examples described herein.

The techniques described herein may be supported by various configurations of the computing device 1302 and are not limited to the specific examples of the techniques described herein. This functionality may also be implemented all or in part through use of a distributed system, such as over a "cloud" 1314 as described below.

The cloud 1314 includes and/or is representative of a platform 1316 for resources 1318. The platform 1316 abstracts underlying functionality of hardware (e.g., servers) and software resources of the cloud 1314. The resources 1318 may include applications and/or data that can be utilized while computer processing is executed on servers that are remote from the computing device 1302. Resources 1318 can also include services provided over the Internet and/or through a subscriber network, such as a cellular or Wi-Fi network.

The platform 1316 may abstract resources 1318 and functions to connect the computing device 1302 with other computing devices. The platform may also serve to abstract scaling of resources to provide a corresponding level of scale to encountered demand for the resources that are implemented via the platform. Accordingly, in an interconnected device embodiment, implementation of functionality described herein may be distributed throughout the system 1300. For example, the functionality may be implemented in part on the computing device 1302 as well as via the platform 1316 that abstracts the functionality of the cloud 1314.

Example Clinical Data

The described systems and techniques have been evaluated relative to a prescription eye drop (lifitegrast ophthalmic solution 5%; Xiidra) as part of a Phase 2 Randomized Clinical Trial. Xiidra is FDA approved for treatment of dry eye syndrome. The Clinical Trial included 40 patients with 20 patients treated using the described systems and techniques and 20 patients treated using Xiidra as indicated. Results of the Clinical Trial conclude that the described systems and techniques and Xiidra are similar in effectiveness in treatment of dry eye syndrome. The time to endpoint was three weeks for the described systems and techniques and the time to endpoint was five weeks for Xiidra. In an interim analysis of the first 22 eyes randomized into the study, the described systems and techniques performed better than Xiidra when evaluated using best corrected visual acuity (BCVA), Hyperemia, fluorescent-antibody (FA) stain, and Lissamine green stain. Vision improvement is considered the best indicator of global effect on dry eyes. BVCA improved 91 percent for patients treated using Xiidra as indicated. BVCA improved 151 percent for patients treated using the described systems and techniques. Thus, during an interim analysis visual acuity improved significantly more in patients treated using the described systems and techniques than in patients treated using Xiidra in the Clinical Trial.

Conclusion

Although implementations systems for management of dry eye syndrome have been described in language specific to structural features and/or methods, it is to be understood that the appended claims are not necessarily limited to the specific features or methods described. Rather, the specific features and methods are disclosed as example implementations of systems for management of dry eye syndrome, and other equivalent features and methods are intended to be within the scope of the appended claims. Further, various different examples are described and it is to be appreciated that each described example can be implemented independently or in connection with one or more other described examples.

What is claimed is:

1. A method for management of dry eye syndrome, the method comprising:
   determining, by a computing device, a palpebral fissure width as a total distance between a medial canthus and a lateral canthus of closed eyelids of an eye;
   generating, by the computing device, an ideal eyelash length based on the total distance, the ideal eyelash length in a range of 20.0 percent to 40.0 percent of the total distance;
   segmenting eyelashes of an upper eyelid of the closed eyelids into a first region and a second region;
   attaching a first prosthesis having the ideal eyelash length to a candidate eyelash of the first region, the first prosthesis including a first channel having a first channel width configured to house the candidate eyelash of the first region; and
   attaching a second prosthesis having a length that differs from the ideal eyelash length to a candidate eyelash of the second region, the second prosthesis including a second channel having a second channel width configured to house the candidate eyelash of the second region, the first prosthesis and the second prosthesis configured to disrupt airflow incident to a tear film of the eye.

2. The method as described in claim 1, wherein the second prosthesis length is less than the ideal eyelash length.

3. The method as described in claim 1, wherein the second prosthesis length is greater than the ideal eyelash length.

4. The method as described in claim 1, further comprising:
   segmenting the eyelashes of the upper eyelid into a third region; and
   attaching a third prosthesis to a candidate eyelash of the third region.

5. The method as described in claim 4, wherein the third prosthesis has a length that is greater than the ideal eyelash length and wherein the second prosthesis length is less than the ideal eyelash length.

6. The method as described in claim 4, wherein the first region is disposed between the second region and the third region.

7. The method as described in claim 4, further comprising:
   segmenting the eyelashes of the upper eyelid into a fourth region; and
   attaching a fourth prosthesis to a candidate eyelash of the fourth region.

8. The method as described in claim 1, wherein the first prosthesis has a width in a range of 0.01 to 0.5 millimeters.

9. The method as described in claim 1, wherein the first prosthesis is attached to the candidate eyelash of the first region by an adhesive.

10. A method for management of dry eye syndrome comprising:
    determining, by a computing device, a distance between a medial canthus and a lateral canthus of eyelids of an eye;
    generating, by the computing device, an ideal eyelash length that represents a percentage of the distance, the ideal eyelash length less than the distance;
    segmenting eyelashes of a lower eyelid of the eyelids into a first region and a second region;
    attaching a first prosthesis to a candidate eyelash of the first region via a first channel having a first channel width configured to house the candidate eyelash of the first region, the first prosthesis having the ideal eyelash length; and
    attaching a second prosthesis having a length that differs from the ideal eyelash length to a candidate eyelash of the second region via a second channel having a second channel width configured to house the candidate eyelash of the second region, the first prosthesis and the second prosthesis configured to generate one or more turbulences to airflow incident to a tear film of the eye.

11. The method as described in claim 10, wherein the candidate eyelash of the first region has a proximal end and a distal end, the first prosthesis has a proximal end and a distal end, and the first prosthesis is configured to overlay the candidate eyelash of the first region via the first channel such that the proximal end of the first prosthesis extends past a proximal end of the candidate eyelash of the first region.

12. The method as described in claim 10, wherein the first prosthesis is configured to house the candidate eyelash of the first region and at least one additional candidate eyelash of the first region via the first channel.

13. The method as described in claim 10, wherein the first prosthesis has a proximal end and a distal end, the first prosthesis decreasing in width from the proximal end to the distal end.

14. The method as described in claim 10, wherein the length of the second prosthesis is based in part on the one or more turbulences, the ideal eyelash length of the first prosthesis, and a configuration of the first prosthesis in the first region and the second prosthesis in the second region.

15. The method as described in claim 10, wherein the ideal eyelash length is based on the distance between the medial canthus and the lateral canthus and a scaling constant, the scaling constant in a range of 0.20 to 0.45.

16. The method as described in claim 10, wherein the ideal eyelash length is in a range of 20.0 percent to 40.0 percent of the distance between the medial canthus and the lateral canthus.

17. A method for management of dry eye syndrome comprising:
    determining, by a computing device, a distance between a medial canthus and a lateral canthus of an eyelid of an eye;
    generating, by the computing device, an ideal eyelash length that represents a percentage of the distance, the ideal eyelash length less than the distance;
    segmenting eyelashes of the eyelid into a first region and a second region;
    attaching a first prosthesis having the ideal eyelash length to a candidate eyelash of the first region via a first sleeve portion configured to envelop the candidate eyelash of the first region; and
    attaching a second prosthesis having a length that differs from the ideal eyelash length to a candidate eyelash of the second region via a second sleeve portion configured to envelop the candidate eyelash of the second region, the first prosthesis and the second prosthesis configured to generate one or more turbulences to airflow incident to a tear film of the eye.

18. The method as described in claim 17, wherein the first prosthesis length is based in part on a proximity of a distal end of the first prosthesis to the eyelid.

19. The method as described in claim 17, wherein one or more of the first prosthesis or the second prosthesis includes a surface modified by a micro-abrasive process to increase an amount of surface area in contact with one or more of the candidate eyelash of the first region or the candidate eyelash of the second region.

20. The method as described in claim 17, wherein one or more of the first prosthesis or the second prosthesis has a tapered geometry.

* * * * *